US012805774B2

(12) United States Patent
Scofield et al.

(10) Patent No.: US 12,805,774 B2
(45) Date of Patent: Nov. 24, 2026

(54) ARCHITECTURE OF A PHOTONIC INTEGRATED CIRCUIT (PIC) AND METHOD FOR OPERATING THE SAME AS WELL AS AN OPTICAL COUPLER

(71) Applicant: ROCKLEY PHOTONICS LIMITED, Altrincham (GB)

(72) Inventors: Adam Scofield, Los Angeles, CA (US); Babak Bahari, Pasadena, CA (US); Abu Thomas, Oak Park, CA (US); Andrea Trita, Pasadena, CA (US); Aaron John Zilkie, Pasadena, CA (US)

(73) Assignee: Rockley Photonics Limited, Altrincham (GB)

( * ) Notice: Subject to any disclaimer, the term of this patent is extended or adjusted under 35 U.S.C. 154(b) by 1002 days.

(21) Appl. No.: 18/056,666

(22) Filed: Nov. 17, 2022

(65) Prior Publication Data

US 2023/0225643 A1 Jul. 20, 2023

Related U.S. Application Data

(60) Provisional application No. 63/280,989, filed on Nov. 18, 2021.

(51) Int. Cl.
*A61B 5/1455* (2006.01)
*A61B 5/0205* (2006.01)
(Continued)

(52) U.S. Cl.
CPC ........ *A61B 5/14552* (2013.01); *A61B 5/0205* (2013.01); *A61B 5/14546* (2013.01); *A61B 5/02427* (2013.01); *A61B 2562/0242* (2013.01)

(58) Field of Classification Search
CPC ... A61B 5/0059; A61B 5/0075; A61B 5/0205; A61B 5/02427; A61B 5/1455;
(Continued)

(56) References Cited

U.S. PATENT DOCUMENTS 5,243,983 A 9/1993 Tarr et al.
5,830,132 A 11/1998 Robinson
(Continued)

FOREIGN PATENT DOCUMENTS

CN 108709847 A 10/2018
EP 3 002 568 A1 4/2016
(Continued)

OTHER PUBLICATIONS

Akram, M. N. et al., "Laser speckle reduction due to spatial and angular diversity introduced by fast scanning micromirror", Applied Optics, Jun. 4, 2010, pp. 3297-3304, vol. 49, No. 17, Optical Society of America.

(Continued)

*Primary Examiner* — Chu Chuan Liu
(74) *Attorney, Agent, or Firm* — Womble Bond Dickinson (US) LLP

(57) ABSTRACT

The invention refers to a photonic integrated circuit (PIC), the photonic integrated circuit comprising: at least one laser, the laser having a laser output, a measuring portion including a measuring port and configured to measure an intensity and/or wavelength of light input at the measuring port, and an output portion configured to output light from the photonic integrated circuit to the portion of the tissue, wherein optionally the laser includes a ring resonator laser, a laser generating light having a fixed wavelength, a laser being constructed using hybrid integration, and/or a tunable laser.

17 Claims, 7 Drawing Sheets

(51) Int. Cl.
*A61B 5/145* (2006.01)
*A61B 5/024* (2006.01)

(58) Field of Classification Search
CPC ........... A61B 5/14551; A61B 5/14552; A61B 5/14532; A61B 5/14546; A61B 5/68; A61B 5/6801; A61B 5/6802; A61B 2562/02; A61B 2562/0242
See application file for complete search history.

(56) References Cited

U.S. PATENT DOCUMENTS

| | | | | |
|---|---|---|---|---|
| 6,246,892 | B1 | 6/2001 | Chance | |
| 6,560,478 | B1 | 5/2003 | Alfano et al. | |
| 6,919,549 | B2 | 7/2005 | Bamji et al. | |
| 7,250,317 | B2 | 7/2007 | Heideman | |
| 7,295,783 | B2 | 11/2007 | Singh et al. | |
| 7,375,812 | B2 | 5/2008 | Atia et al. | |
| 7,505,128 | B2 | 3/2009 | Zribi et al. | |
| 7,761,126 | B2 | 7/2010 | Gardner et al. | |
| 7,865,225 | B2 | 1/2011 | Kaltschmidt et al. | |
| 8,237,927 | B1 | 8/2012 | Reeve et al. | |
| 8,376,955 | B2 | 2/2013 | Baker, Jr. | |
| 8,923,942 | B2 | 12/2014 | Bernreuter | |
| 9,494,567 | B2 | 11/2016 | Islam | |
| 9,772,280 | B2 | 9/2017 | Cerussi et al. | |
| 9,804,027 | B2 | 10/2017 | Fish et al. | |
| 9,846,126 | B2 | 12/2017 | Gunn, III et al. | |
| 9,848,787 | B2 | 12/2017 | White et al. | |
| 10,215,698 | B2 | 2/2019 | Han et al. | |
| 10,241,033 | B2 | 3/2019 | Uematsu et al. | |
| 10,326,035 | B2 | 6/2019 | Lu et al. | |
| 10,326,036 | B2 | 6/2019 | Sweeney et al. | |
| 10,352,768 | B2 | 7/2019 | Simpkin et al. | |
| 10,357,165 | B2 | 7/2019 | Yoon | |
| 10,411,430 | B1 * | 9/2019 | Koch | H01S 3/10061 |
| 10,422,693 | B2 | 9/2019 | Fish et al. | |
| 10,451,537 | B2 | 10/2019 | Nakaji | |
| 10,463,286 | B2 | 11/2019 | Schenkman et al. | |
| 10,568,527 | B2 | 2/2020 | Yoon et al. | |
| 10,627,849 | B1 | 4/2020 | Scofield et al. | |
| 10,641,962 | B2 | 5/2020 | Nykänen et al. | |
| 10,643,903 | B2 | 5/2020 | Drake et al. | |
| 10,677,989 | B2 | 6/2020 | Abediasl et al. | |
| 10,684,114 | B2 | 6/2020 | Li et al. | |
| 10,718,668 | B2 | 7/2020 | Gu et al. | |
| 10,739,256 | B1 | 8/2020 | Rickman et al. | |
| 10,750,956 | B2 | 8/2020 | Zalevsky et al. | |
| 10,775,239 | B2 | 9/2020 | Lee et al. | |
| 11,022,751 | B2 | 6/2021 | Bauters et al. | |
| 11,045,103 | B2 | 6/2021 | Shchekin et al. | |
| 11,079,364 | B2 | 8/2021 | Leger et al. | |
| 11,096,608 | B2 | 8/2021 | Van Dorpe et al. | |
| 2005/0249509 | A1 | 11/2005 | Nagarajan et al. | |
| 2006/0124829 | A1 | 6/2006 | Song et al. | |
| 2006/0204175 | A1 | 9/2006 | Laurent-Lund et al. | |
| 2008/0204752 | A1 | 8/2008 | Dorvee et al. | |
| 2008/0220512 | A1 | 9/2008 | Koh et al. | |
| 2008/0316567 | A1 | 12/2008 | Grasser et al. | |
| 2010/0049017 | A1 * | 2/2010 | LeBoeuf | A61B 5/6826 356/300 |
| 2014/0376001 | A1 | 12/2014 | Swanson | |
| 2015/0196251 | A1 | 7/2015 | Outwater et al. | |
| 2016/0066790 | A1 | 3/2016 | Shcherbakov et al. | |
| 2016/0106327 | A1 | 4/2016 | Yoon et al. | |
| 2016/0161685 | A1 | 6/2016 | Xu et al. | |
| 2016/0266337 | A1 | 9/2016 | Feng | |
| 2016/0278676 | A1 | 9/2016 | Eisen et al. | |
| 2016/0282265 | A1 | 9/2016 | Su et al. | |
| 2017/0108439 | A1 | 4/2017 | Stievater et al. | |
| 2017/0138789 | A1 | 5/2017 | Ivanov | |
| 2017/0222398 | A1 * | 8/2017 | Zilkie | H01S 5/141 |
| 2017/0315292 | A1 | 11/2017 | Mullen et al. | |
| 2018/0045566 | A1 | 2/2018 | Fish et al. | |
| 2018/0238794 | A1 | 8/2018 | Kangas et al. | |
| 2018/0283950 | A1 | 10/2018 | Ge et al. | |
| 2018/0296168 | A1 * | 10/2018 | Rice | A61B 5/7278 |
| 2019/0053721 | A1 | 2/2019 | Boas et al. | |
| 2019/0094009 | A1 | 3/2019 | Aizawa et al. | |
| 2019/0336006 | A1 | 11/2019 | Horstmeyer et al. | |
| 2019/0391243 | A1 | 12/2019 | Nicolaescu | |
| 2019/0391702 | A1 | 12/2019 | Jo et al. | |
| 2020/0003619 | A1 | 1/2020 | Hu et al. | |
| 2020/0069225 | A1 | 3/2020 | Vizbaras et al. | |
| 2020/0158548 | A1 | 5/2020 | Rice et al. | |
| 2020/0196874 | A1 | 6/2020 | Rozental et al. | |
| 2020/0359948 | A1 | 11/2020 | Dunn et al. | |
| 2020/0397351 | A1 | 12/2020 | Miyata | |
| 2021/0022623 | A1 | 1/2021 | Rice et al. | |
| 2021/0028602 | A1 | 1/2021 | Cao et al. | |
| 2022/0370010 | A1 | 11/2022 | Zilkie et al. | |
| 2022/0413143 | A1 | 12/2022 | Parsa et al. | |
| 2023/0003938 | A1 | 1/2023 | Zilkie et al. | |
| 2023/0039055 | A1 | 2/2023 | Gardner et al. | |

FOREIGN PATENT DOCUMENTS

| | | | |
|---|---|---|---|
| WO | WO 2019/149815 | A1 | 8/2019 |
| WO | WO 2020/030641 | A1 | 2/2020 |
| WO | WO 2021/058338 | A1 | 4/2021 |
| WO | WO 2021/094473 | A1 | 5/2021 |
| WO | WO 2021/116766 | A1 | 6/2021 |
| WO | WO 2021/116766 | A8 | 6/2021 |

OTHER PUBLICATIONS

Baek, H. J. et al., "The Effect of Optical Crosstalk on Accuracy of Reflectance-Type Pulse Oximeter for Mobile Healthcare", Journal of Healthcare Engineering, Oct. 21, 2018, 9 pages, vol. 2018, Article ID 3521738, Hindawi, https://doi.org/10.1155/2018/3521738.

Baets, R. et al., "Spectroscopy-on-chip applications of silicon photonics", Proc. of SPIE, 2013, pp. 862701-1 through 862701-10, vol. 8627, SPIE.

Berger, A. J. et al., "Feasibility of measuring blood glucose concentration by near-infrared Raman spectroscopy", Spectrochimica Acta Part A, 1997, pp. 287-292, Elsevier Science B.V.

Bi, R. et al., "A speckle-based method for fast blood flow measurement in deep tissue", Proceedings of SPIE, Optical Biopsy XIX: Toward Real-Time Spectroscopic Imaging and Diagnosis, Mar. 5, 2021, pp. 1163606-1 through 1163606-5, vol. 11636, SPIE.

Biswas, A. et al., "Fast diffuse correlation spectroscopy with a low-cost, fiber-less embedded diode laser", Biomedical Optics Express, Oct. 4, 2021, pp. 6686-6700, vol. 12, No. 11, Optical Society of America.

Brouckaert, J. et al., "Silicon-on-Insulator Microspectrometer", Proceedings Symposium IEEE/LEOS Benelux Chapter, 2008, pp. 7-10, IEEE.

Cole, D. B. et al., "Integrated heterodyne interferometer with on-chip modulators and detectors", Optics Letters, Jun. 25, 2015, pp. 3097-3100, vol. 40, No. 13, Optical Society of America.

Epping, J. P. et al., "High power, tunable, narrow linewidth dual gain hybrid laser", Laser Congress, Oct. 3, 2019, pp. 1-2.

Fu, D. et al., "In Vivo Metabolic Fingerprinting of Neutral Lipids with Hyperspectral Stimulated Raman Scattering Microscopy", Journal of the American Chemical Society, May 28, 2014, pp. 8820-8828, American Chemical Society Publications.

Fukui, T. et al., "Single-Pixel Imaging Using Multimode Fiber and Silicon Photonic Phased Array", Journal of Lightwave Technology, Jul. 14, 2020, pp. 839-844, vol. 39, No. 3, IEEE.

Ge, Z. et al., "Dynamic laser speckle analysis using the event sensor", Applied Optics, Dec. 23, 2020, pp. 172-178, vol. 60, No. 1, Optical Society of America.

Ghijsen, M. et al., "Wearable speckle plethysmography (SPG) for characterizing microvascular flow and resistance", Biomedical Optics Express, Jul. 30, 2018, pp. 3937-3952, vol. 9, No. 8, Optical Society of America.

Gottschling, K. et al., "Molecular Insights into Carbon Dioxide Sorption in Hydrazone-Based Covalent Organic Frameworks with

(56) References Cited

OTHER PUBLICATIONS

Tertiary Amine Moieties", Chemistry of Materials, Feb. 13, 2019, pp. 1946-1955, American Chemical Society.
Hashimoto, Y. et al., "Fabrication of an Anti-Reflective and Super-Hydrophobic Structure by Vacuum Ultraviolet Light-Assisted Bonding and Nanoscale Pattern Transfer", Micromachines, Apr. 15, 2018, pp. 1-11, www.mdpi.com/journal/micromachines.
Hollis, V. S. et al., "Non-invasive monitoring of brain tissue temperature by near-infrared spectroscopy", Proceedings of SPIE, Optical Tomography and Spectroscopy of Tissue IV, Jun. 29, 2001, pp. 470-481, vol. 4250, SPIE, https://www.spiedigitallibrary.org/conference-proceedings-of-spie/4250/1/Noninvasive-monitoring-of-brain-tissue-temperature-by-near-infrared-spectroscopy/10.1117/12.434506.short?SSO=1.
International Search Report and Written Opinion of the International Searching Authority, Mailed Mar. 11, 2021, Corresponding to PCT/IB2020/001037, 13 pages.
International Search Report and Written Opinion of the International Searching Authority, mailed Apr. 4, 2023, corresponding to PCT/EP2022/082341, 33 pages.
International Search Report and Written Opinion of the International Searching Authority, mailed Feb. 1, 2022, corresponding to PCT/IB2021/000649, 18 pages.
International Search Report and Written Opinion of the International Searching Authority, mailed Feb. 14, 2023, corresponding to PCT/EP2022/082162, 33 pages.
International Search Report and Written Opinion of the International Searching Authority, mailed Nov. 15, 2021, corresponding to PCT/IB2021/000517, 15 pages.
International Search Report and Written Opinion of the International Searching Authority, mailed Oct. 10, 2022, corresponding to PCT/IB2022/000373, 16 pages.
International Search Report and Written Opinion of the International Searching Authority, mailed Oct. 19, 2022, corresponding to PCT/EP2022/071467, 16 pages.
Invitation to Pay Additional Fees and Partial Search Report mailed Feb. 14, 2023 in related International Application No. PCT/EP2022/082341, 18 pages.
Izutsu, M. et al., "Integrated Optical SSB Modulator/Frequency Shifter", IEEE Journal of Quantum Electronics, Nov. 1981, pp. 2225-2227, vol. QE-17, No. 11, IEEE.
Kang, J. W. et al., "Direct observation of glucose fingerprint using in vivo Raman spectroscopy," Science Advances, Jan. 24, 2020, pp. 1-8, American Association for the Advancement of Science.
Karlsson, C. J. et al., "All-fiber multifunction continuous-wave coherent laser radar at 1.55 μm for range, speed, vibration, and wind measurements", Applied Optics, Jul. 20, 2000, pp. 3716-3726, vol. 39, No. 21, Optical Society of America.
Lai, M. et al., "Perfusion Monitoring by Contactless Photoplethysmography Imaging", 2019 IEEE 16th International Symposium on Biomedical Imaging (ISBI 2019), Venice, Italy, Apr. 8-11, 2019, pp. 1778-1782, IEEE.
Lai, N. et al., "CO2 Capture With Absorbents of Tertiary Amine Functionalized Nano-SiO2", Frontiers in Chemistry, Feb. 28, 2020, pp. 1-9, vol. 8, Article 146, www.frontiersin.org.
Lapchuk, A. et al., "Investigation of speckle suppression beyond human eye sensitivity by using a passive multimode fiber and a multimode fiber bundle", Applied Optics, Feb. 21, 2020, pp. 6820-6834, vol. 28, No. 5, Optical Society of America.
Liu, X. et al., "Simultaneous measurements of tissue blood flow and oxygenation using a wearable fiber-free optical sensor", Journal of Biomedical Optics, Jan. 29, 2021, pp. 012705-1 through 012705-15, vol. 26, No. 1, SPIE.
Loi, R. et al., "Transfer Printing of AlGaInAs/InP Etched Facet Lasers to Si Substrates", IEEE Photonics Journal, Nov. 11, 2016, 11 pages, vol. 8, No. 6, IEEE.
Lu, H. et al., "Single-trial estimation of the cerebral metabolic rate of oxygen with imaging photoplethysmography and laser speckle contrast imaging", Optics Letters, Mar. 17, 2015, pp. 1193-1196, vol. 40, No. 7, Optical Society of America.
Mehta, D. S. et al., "Laser speckle reduction by multimode optical fiber bundle with combined temporal, spatial, and angular diversity", Applied Optics, Apr. 11, 2012, pp. 1894-1904, vol. 51, No. 12, Optical Society of America.
Merritt, S. et al., "Monitoring temperature non-invasively using broadband Diffuse Optical Spectroscopy", OSA/FIO, 2004, 1 page, Optical Society of America, https://opg.optica.org/abstract.cfm?URI=FiO-2004-FTuK4.
Noriki, A. et al., "45-degree curved micro-mirror for vertical optical I/O of silicon photonics chip", Optics Express, Jul. 1, 2019, pp. 19749-19757, vol. 27, No. 14, Optical Society of America, https://doi.org/10.1364/OE.27.019749.
Poulton, C. V. et al., "Frequency-modulated Continuous-wave LIDAR Module in Silicon Photonics", OFC, 2015, 4 pages, Optical Society of America.
Redding, B. et al., "Compact spectrometer based on a disordered photonic chip", Nature Photonics, Jul. 28, 2013, pp. 746-751, vol. 7, Macmillan Publishers Limited.
Redding, B. et al., "Evanescently coupled multimode spiral spectrometer", Optica, Aug. 25, 2016, pp. 956-962, vol. 3, No. 9, Optical Society of America.
Robinson, M. B., "Interferometric diffuse correlation spectroscopy improves measurements at long source-detector separation and low photon count rate", Journal of Biomedical Optics, Sep. 30, 2020, pp. 097004-1 through 097004-12, vol. 25, No. 9, SPIE.
Roelkens, G. et al., "Transfer printing for silicon photonics transceivers and interposers", 2018 IEEE Optical Interconnects Conference, Jun. 4, 2018, pp. 13-14, IEEE.
Ryckeboer, E., "Spectroscopic Detection of Glucose with a Silicon Photonic Integrated Circuit", Universiteit Gent, Jan. 1, 2014, 263 pages, ISBN 978-90-8578-688-7, http://www.photonics.intec.ugent.be/download/phd_206.pdf.
Schneider, S. et al., "Optical coherence tomography system mass-producible on a silicon photonic chip", Optics Express, Jan. 20, 2016, pp. 1573-1586, vol. 24, No. 2, Optical Society of America.
Shimotsu, S. et al., "Single Side-Band Modulation Performance of a LiNbO3 Integrated Modulator Consisting of Four-Phase Modulator Waveguides", IEEE Photonics Technology Letters, Apr. 2001, pp. 364-366, vol. 13, No. 4, IEEE.
Subramanian, A. Z. et al., "Silicon and silicon nitride photonic circuits for spectroscopic sensing on-a-chip [Invited]", Photon. Res., Aug. 28, 2015, pp. B47-B59, vol. 3, No. 5, Chinese Laser Press.
Timm, U. et al., "Non-Invasive Optical Real-time Measurement of Total Hemoglobin Content", Procedia Engineering, 2010, pp. 488-491, Elsevier Ltd.
Tran, T-T-K. et al., "Speckle reduction in laser projection displays through angle and wavelength diversity", Applied Optics, Feb. 16, 2016, pp. 1267-1274, vol. 55, No. 6, Optical Society of America.
Tuchin, V., "Chapter 8: Coherent Effects at the Interaction of Laser Radiation with Tissues and Cell Flows", Tissue Optics Light Scattering Methods and Instruments for Medical Diagnostics, 3rd Edition, 2015, pp. 359-417, SPIE.
U.S. Appl. No. 17/711,974, filed Apr. 1, 2022.
U.S. Appl. No. 17/934,502, filed Sep. 22, 2022.
U.S. Appl. No. 18/019,085, filed Jan. 31, 2023.
U.S. Appl. No. 18/027,881, filed Mar. 22, 2023.
U.S. Notice of Allowance from U.S. Appl. No. 17/757,130, dated Jan. 18, 2023, 10 pages.
Valley, G.C. et al., "Multimode waveguide speckle patterns for compressive sensing", Optics Letters, May 23, 2016, pp. 2529-2532, vol. 41, No. 11, Optical Society of America.
Van Gastel, M. et al., "Camera-based pulse-oximetry—validated risks and opportunities from theoretical analysis", Biomedical Optics Express, Dec. 5, 2017, pp. 102-119, vol. 9, No. 1, Optical Society of America.
Website: "Optical Solutions", Molex, dated 2023, printed May 10, 2023, 13 pages, Molex, LLC, https://www.molex.com/en-us/products/optical-solutions.
Website: "Track Your SpO2 to Uncover Changes in Your Wellbeing", Fitbit News, dated Sep. 7, 2020, printed Apr. 17, 2023, 7 pages, Fitbit, Inc., https://blog.fitbit.com/track-your-spo2/).

(56) References Cited

OTHER PUBLICATIONS

Wenz, J. J., "Examining water in model membranes by near infrared spectroscopy and multivariate analysis", BBA—Biomembranes, Dec. 9, 2017, pp. 673-682, Elsevier B.V., https://www.sciencedirect.com/science/article/pii/S0005273617303905.
Xu, M. et al., "Laser Speckle Reduction Using a Motionless Despeckle Element Based on Random Mie Scattering", Journal of Display Technology, Nov. 12, 2013, pp. 151-156, vol. 10, No. 2, IEEE.
Yamakoshi, Y. et al., "Side-scattered finger-photoplethysmography: experimental investigations toward practical noninvasive measurement of blood glucose", Journal of Biomedical Optics, Jun. 2017, pp. 067001-1 through 067001-11, vol. 22, No. 6, SPIE.
Yao, Z. et al., "Integrated Silicon Photonic Microresonators: Emerging Technologies", IEEE Journal of Selected Topics in Quantum Electronics, Jun. 11, 2018, 24 pages, vol. 24, No. 6, IEEE.
Zhang, J. et al., "III-V-on-Si photonic integrated circuits realized using micro-transfer-printing", APL Photonics, Nov. 4, 2019, pp. 110803-1 through 110803-10.
Zijlstra, W. G. et al., "Absorption Spectra of Human Fetal and Adult Oxyhemoglobin, De-Oxyhemoglobin, Carboxyhemoglobin, and Methemoglobin", Clinical Chemistry, Sep. 1991, pp. 1633-1638, vol. 37, No. 9, https://academic.oup.com/clinchem/article-abstract/37/9/1633/5649610?redirectedFrom=fulltext.
Zilkie, A. J. et al., "Multi-Micron Silicon Photonics Platform for Highly Manufacturable and Versitile Photonic Integrated Circuits", IEEE Journal of Selected Topics in Quantum Electronics, Apr. 15, 2019, 13 pages, vol. 25, No. 5, IEEE.
Zilkie, A. J. et al., "Power-efficient III-V/Silicon external cavity DBR lasers", Optics Express, Sep. 27, 2012, pp. 23456-23462, vol. 20, No. 21, Optical Society of America.
European Patent Office Communication pursuant to Article 94(3) EPC, for Patent Application No. 22 818 681.3, mailed Jul. 28, 2025, 6 pages.

* cited by examiner

ARCHITECTURE OF A PHOTONIC INTEGRATED CIRCUIT (PIC) AND METHOD FOR OPERATING THE SAME AS WELL AS AN OPTICAL COUPLER

CROSS-REFERENCE TO RELATED APPLICATION(S)

The present application claims priority to and the benefit of U.S. Provisional Application No. 63/280,989, filed Nov. 18, 2021, entitled "Architecture of a photonic integrated circuit (PIC) and method for operating the same", the entire content of which is incorporated herein by reference.

The present application also makes reference to International Application No. PCT/IB2022/000373 filed Jun. 24, 2022, entitled "TRANSMITTER PHOTONIC INTEGRATED CIRCUIT", the entire content of which is incorporated herein by reference. The present application makes reference to International application published as WO 2021/116766, filed on Dec. 11, 2020, entitled "OPTICAL SENSING MODULE" which is incorporated by reference in its entirety.

The present application makes reference to U.S. application Ser. No. 17/814,787, filed on Jul. 25, 2022, entitled "PHOTONIC INTEGRATED CIRCUIT", the entire content of which is incorporated herein by reference, and International Application No PCT/EP2022/071467, filed on Jul. 29, 2022, entitled "PHOTONIC INTEGRATED CIRCUIT", the entire content of which is incorporated herein by reference.

The present application makes reference to U.S. application Ser. No. 17/711,974, filed on Apr. 1, 2022, entitled "OPTICAL SENSOR MODULES", the entire content of which is incorporated herein by reference

TECHNICAL FIELD

The invention refers to a photonic integrated circuit (PIC) for optically investigating flowing and/or non-flowing liquids, for example, flowing blood at a portion of tissue. The invention also refers to a method for controlling a photonic integrated circuit (PIC) for optically investigating flowing and/or non-flowing liquids.

The invention further relates to an optical coupler between a first optical element and a second optical element.

BACKGROUND

Digital healthcare is transforming the healthcare industry with a rising demand for real-time and on-demand analysis of various biomarkers for a range of purposes. Wearable devices ("wearables") are now commonplace in the fields of wellness and healthcare (including for e.g. fitness tracking, general health monitoring, and medical condition management). For devices such as these, there is a desire for the sensing and measuring of biological parameters to be quick, non-invasive and of sufficient specificity, sensitivity, and accuracy. As a result, there is a desire to provide components suitable for use in non-invasive wearable devices that provide the necessary technical requirements for the biological parameters that are to be measured, but also that are conveniently small and that can be manufactured at a consumer-friendly price point. Whilst, for the visible and NIR (up to 1200 nm) wavelength ranges LEDs have been used, in the IR wavebands lasers have been introduced with the benefits of narrow bandwidths and higher intensities (better S/N ratios). It is known that non-invasive sensing modules may find uses outside of the wearable device market, for example in robotics or remote sensing.

Wearable devices should be robust, reliable and easy to wear and may include skin contact patches, wrist watches, rings, ear buds, head bands, and glasses frames.

SUMMARY

This invention can be relevant to the application of lasers on spectroscopy chips for use in the visible and NIR wavelength range.

A photonic integrated circuit (PIC) may be configured to optically investigate blood flow and blood volume changes, and/or measurements of pulse oximetry (SpO2), oxygen saturation, carboxy haemoglobin, methaemoglobin, or fractional oxygen saturation at a portion of tissue of a user. However, the photonic integrated circuit may be used for other applications, such as a Lab-on-a-Chip, for measuring other types of fluids and/or gases, for Raman spectroscopy, and/or any other type of spectroscopy measurements. Pulse oximetry (SpO2), oxygen saturation, carboxy haemoglobin, methaemoglobin, or fractional oxygen saturation are described in WO 2021/116766, filed on Dec. 11, 2020, entitled "OPTICAL SENSING MODULE" which is incorporated by reference in its entirety.

In an optional embodiment, one, more, or all optical components, such as waveguides, light sources, and the like, disclosed in WO 2021/116766 may be configured to transmit, convey, and/or are functional for light having wavelength below 1200 nm, below 1000 nm, below 850 nm, and/or 750 nm. For example, the optical components disclosed in WO 2021/116766 may include silicon nitride ($Si_3N_4$).

One example would be the application of the photonic integrated circuit for the applications as described in International Application No. PCT/IB2022/000373 filed Jun. 24, 2022, entitled "TRANSMITTER PHOTONIC INTEGRATED CIRCUIT", the entire content of which is incorporated herein by reference. The photonic integrated circuit may be the transmitter photonic integrated circuit for generating an optical signal for optical spectroscopy of a surface as described in PCT/IB2022/000373. The one or more coherent light sources described in PCT/IB2022/000373 can correspond to the lasers discussed below.

In an optional embodiment, one, more, or all optical components, such as waveguides, light sources, and the like, disclosed in PCT/IB2022/000373 may be configured to transmit, convey, and/or are functional for light having wavelength below 1200 nm, below 1000 nm, below 850 nm, and/or 750 nm. For example, the optical components disclosed in PCT/IB2022/000373 may include silicon nitride ($Si_3N_4$).

A further example would be the application of the photonic integrated circuit for generating an optical signal for optical spectroscopy of a surface (e.g. skin). Typically, the transmitter PIC would be used in conjunction with a receiver for receiving light that has been scattered and/or reflected from the surface being studied by spectroscopy. The photonic integrated circuit may be the transmitter photonic integrated circuit for generating an optical signal for optical spectroscopy of a surface.

For example, the homogenizer described in PCT/IB2022/000373 may be used with the receiver. Further, the speckle mitigation techniques, such as the ones described in described in PCT/IB2022/000373, may be capable of being turned on and off and not permanently employed to address the fact that some techniques benefit from coherent light while others benefit from incoherent or spatially homogenized light.

A further example would be the application of the photonic integrated circuit for the applications as described in U.S. application Ser. No. 17/814,787, filed on Jul. 25, 2022, entitled "PHOTONIC INTEGRATED CIRCUIT", the entire content of which is incorporated herein by reference, and/or PCT application No PCT/EP2022/071467, filed on Jul. 29, 2022, entitled "PHOTONIC INTEGRATED CIRCUIT", the entire content of which is incorporated herein by reference. The photonic integrated circuit may be the photonic integrated circuit (PIC) for optically investigating blood flow at a portion of tissue of a user as described in U.S. application Ser. No. 17/814,787 and/or PCT/EP2022/071467. The laser described in U.S. application Ser. No. 17/814,787 and/or PCT/EP2022/071467 can correspond to the lasers discussed below.

In an optional embodiment, one, more, or all optical components, such as waveguides, light sources, and the like, disclosed in U.S. application Ser. No. 17/814,787 and/or PCT/EP2022/071467 may be configured to transmit, convey, and/or are functional for light having wavelength below 1200 nm, below 1000 nm, below 850 nm, and/or 750 nm. For example, the optical components disclosed in U.S. application Ser. No. 17/814,787 and/or PCT/EP2022/071467 may include silicon nitride ($Si_3N_4$).

Further, examples of optical sensors (such as optical sensor module for measuring both speckleplethysmography (SPG) and photoplethysmography (PPG)) for analysing the light generated by photonic integrated circuit and subsequently reflected, diffracted, and/or absorbed light by a sample or object of interest (e.g. human tissue) are described in U.S. application Ser. No. 17/711,974, filed on Apr. 1, 2022, entitled "OPTICAL SENSOR MODULES", the entire content of which is incorporated herein by reference The photonic integrated circuit may be the photonic integrated circuit (PIC) for optically investigating blood flow at a portion of tissue of a user. A photonic integrated chip/circuit (PIC) for optically investigating blood flow at a portion of tissue of a user may comprise a laser, the laser providing an optical output, a first component of which is transmitted to the portion of tissue; one or more detectors, each detector configured to receive speckle generated at the portion of tissue; wherein the PIC further comprises one or more optical splitter(s) to optically couple a second component of the optical output of the laser to one or more respective input(s) of the one or more detectors; and wherein temporal autocorrelation is carried out at the detector between a sample arm formed by the first component and a reference arm formed by the second component. The laser described above can correspond to the lasers discussed below.

According to a first embodiment, a photonic integrated circuit (PIC) comprises at least one laser, a measuring portion including a measuring port and configured to measure an intensity and/or wavelength of light input at the measuring port, and an output portion configured to output light from the photonic integrated circuit to the portion of the tissue. The laser has a laser output. Optionally, the laser includes a ring resonator laser, a laser generating light having a fixed wavelength, a laser being constructed using hybrid integration, and/or a tunable laser. Hybrid integration may relate to an active material which is not monolithically integrated into a Silicon-on-Insulator (SOI). The (optically) active material may be fabricated separately and bonded to the SOI platform wafer.

According to a second embodiment, a method for controlling a photonic integrated circuit (PIC) comprises a) setting a tuning element of a laser,
b) turning the laser on for generating laser light having a wavelength and an intensity,
c) measuring the intensity and/or the wavelength of generated laser light, and
d) detecting the reflection of the generated laser light from the portion of the tissue and analysing the reflected light for investigating the blood flow, wherein optionally the laser includes a ring resonator laser, a laser being constructed using hybrid integration, and/or a tunable laser.

According to a third embodiment, a method for controlling a photonic integrated circuit for optically investigating blood flow at a portion of tissue of a user comprises a) setting a tuning element of one of n tunable lasers, n being an integer greater than or equal to 2,
b) turning the one of the n tunable lasers on for generating laser light having a wavelength and an intensity,
c) measuring the intensity and/or the wavelength of generated laser light,
d) detecting the reflection of the generated laser light from the portion of the tissue and analysing the reflected light for investigating the blood flow, and
e) repeating steps a) to d).

According to a fourth embodiment, an optical coupler comprises a first optical element including a first waveguide and a second optical element including a second waveguide and an end portion.

The first waveguide includes a facet configured to emit electromagnetic radiation from the first optical element. The end portion is configured to couple electromagnetic radiation into the second optical element. The first optical element and a second optical element are fixed so that the facet faces the end portion. The end portion includes a plurality of nanobeams wherein each nanobeam has a width that is smaller than the width of the second waveguide. The end portion includes a merging section at which the nanobeams merge. The optical element further includes a tapered portion arranged between the merging section and the second waveguide. A minimal width of the merging section is smaller than the width of the second waveguide.

In an optional embodiment, the receiver and/or the (optical) detector is arranged separated from the photonic integrated circuit. The photonic integrated circuit and the receiver/detector may be arranged within a common housing or arranged in separate housings.

In an optional embodiment, the photonic integrated circuit may be configured to generate, output, and/or deliver n wavelengths to tissue, wherein optionally the detection of the generated, output, and/or delivered light is provided on a receiver that is not arranged on the photonic integrated circuit. Further optionally, the receiver may include a discreet photodiode or a Complementary metal-oxide-semiconductor (CMOS) image sensor.

In an optional embodiment, the receiver includes one or more optical detectors.

In an optional embodiment, the receiver includes a controllable homogenizer, such as a Micro-Electro-Mechanical Systems (MEMS) membrane, that is configured to selectively turn spatial coherence off and on.

In an optional embodiment of the photonic integrated circuit, the laser includes a ring resonator laser, a laser generating light having a fixed wavelength, a laser being constructed using hybrid integration, and/or a tunable laser.

In an optional embodiment, the photonic integrated circuit further comprises:

n lasers, n being an integer greater than or equal to 2 and each laser has a laser output, and a splitting/combining portion including n input ports, a first output port, and a second output port, each input port being coupled to a respective one of the laser outputs, the first output port being coupled to the measuring port, and the second output port being coupled to the output portion.

In an optional embodiment of the photonic integrated circuit, the splitting/combining portion includes n optical splitters, each optical splitter is coupled to one input port, one first output port, and one second output port.

In an optional embodiment of the photonic integrated circuit, the output portion includes n output channels, each output channel being coupled to one second output port.

In an optional embodiment of the photonic integrated circuit, the splitting/combining portion includes one optical combiner and one optical splitter, the optical combiner being coupled to the n input ports for combining the light of the n lasers, the optical splitter being coupled to the optical combiner, to the first input port, and the second input port for splitting the light received from the optical combiner into the first output port and the second output port.

In an optional embodiment of the photonic integrated circuit, the output portion includes one output channel that is coupled to the optical splitter.

In an optional embodiment of the photonic integrated circuit, the splitting/combining portion includes n optical splitters and one optical combiner, wherein each optical splitter is coupled to one input port, the one optical combiner and to the second output port for splitting the light received from the respective laser into the optical combiner and the second output port, and wherein the optical combiner is coupled to the measuring portion for combining the light received from the n optical splitters.

In an optional embodiment of the photonic integrated circuit, the output portion includes n output channels, each output channel being coupled to a respective one of the optical splitters.

In an optional embodiment, the photonic integrated circuit further comprises a control portion coupled to the n lasers and the measuring portion for tuning the n lasers based on the intensity and/or the wavelength measured by the measuring portion.

In an optional embodiment of the photonic integrated circuit, the control portion tunes all n tunable lasers using a common tuning algorithm.

In an optional embodiment of the photonic integrated circuit, the tunable laser includes a reflective semiconductor optical amplifier (RSOA) and a tuning element, wherein the tuning element includes a micro-ring reflector and/or a sampled Distributed Bragg Reflector (DBR) grating.

In an optional embodiment of the photonic integrated circuit, at least one of the n tunable lasers includes phase control section coupled between the reflective semiconductor optical amplifier (RSOA) and the tuning element for determining the phase of light.

In an optional embodiment of the photonic integrated circuit, the photonic integrated circuit includes a waveguide core made from silicon nitride ($Si_3N_4$), wherein optionally the laser generates light having wavelength below 1000 nm.

In an optional embodiment of the photonic integrated circuit, the laser output is split into a first optical component and a second optical component, wherein the first optical component is arranged to be transmitted to and generate speckle at the portion of tissue of the user;

the photonic integrated circuit further comprising:

one or more detectors, each detector configured to receive the speckle generated by the first optical component at the portion of tissue; and one or more optical splitters optically coupling the second optical component to one or more respective input(s) of the one or more detectors;

wherein the photonic integrated circuit is further adapted to measure interference at the one or more detectors between a sample arm formed by the first optical component and a reference arm formed by the second optical component.

In an optional embodiment of the photonic integrated circuit, the photonic integrated circuit is configured to execute diffuse correlation spectroscopy (DCS).

In an optional embodiment of the photonic integrated circuit, the photonic integrated circuit executes a measurement of pulse oximetry ($SpO_2$), oxygen saturation, carboxy haemoglobin, methaemoglobin, or fractional oxygen saturation.

In an optional embodiment, the photonic integrated circuit further comprises a homogenizer, the homogenizer comprising a planar waveguide device which receives light from the laser and generates interference to produce multiple statistically uncorrelated speckle patterns that are combined to provide the optical output at the output portion.

A wearable device comprises a photonic integrated circuit according to any one of the above embodiments of the photonic integrated circuit.

In an optional embodiment, the method for controlling a photonic integrated circuit includes a) setting a tuning element of one of n lasers, n being an integer greater than or equal to 2, b) turning the one of the n lasers on for generating laser light having a wavelength and an intensity, c) measuring the intensity and/or the wavelength of generated laser light, d) detecting the reflection of the generated laser light from the portion of the tissue and analysing the reflected light for investigating the blood flow, and e) repeating steps a) to d).

In an optional embodiment of the method for controlling a photonic integrated circuit, step a) is executed based on pre-calibrated set points and before step b).

In an optional embodiment of the method for controlling a photonic integrated circuit, step e) is repeated for each one of the n lasers and each wavelength that can be generated by the n lasers.

In an optional embodiment of the method for controlling a photonic integrated circuit, step a) includes simultaneously setting the tuning elements of all n lasers and wherein step e) includes repeating steps b) to d) for each one of the n lasers before returning to step a).

In an optional embodiment of the method for controlling a photonic integrated circuit, step b) is executed before a) and wherein the setting of the tuning element of the one of the n lasers is based on the results achieved in step c).

In an optional embodiment of the method for controlling a photonic integrated circuit, steps a) to d) define a first cycle which includes varying the setting of the tuning element for the one of the n elements and a second cycle of repeating the first cycle which includes changing the one of the n lasers.

In an optional embodiment of the method for controlling a photonic integrated circuit, steps c) and d) are simultaneously executed.

In an optional embodiment of the optical coupler, the width of each of the nanobeams is constant and respective sections of the plurality of nanobeams extend parallel to each other.

In an optional embodiment of the optical coupler, a first angle between a direction of extension of the first waveguide and a plane of the facet is between 80° and 84°, optionally 82°.

In an optional embodiment of the optical coupler, a side surface of the second optical element extends parallel to the facet, wherein a second angle between a direction of extension of the parallel sections of the plurality of nanobeams and a plane of the side surface is between 79° and 83°, optionally 81°.

In an optional embodiment of the optical coupler, the end portion is spaced apart from the side surface of the second optical element, wherein a space between the side surface and the end portion is filled with SiO2.

In an optional embodiment of the optical coupler, the first waveguide includes a T-bar providing the facet.

In an optional embodiment, the photonic integrated circuit further comprises the optical coupler of any one of the embodiments outlined above.

BRIEF DESCRIPTION OF FIGURES

Embodiments of the invention will be discussed in conjunction with the accompanying drawings. Therein.

DESCRIPTION OF SOME EMBODIMENTS OF THE INVENTION

Figure 1:
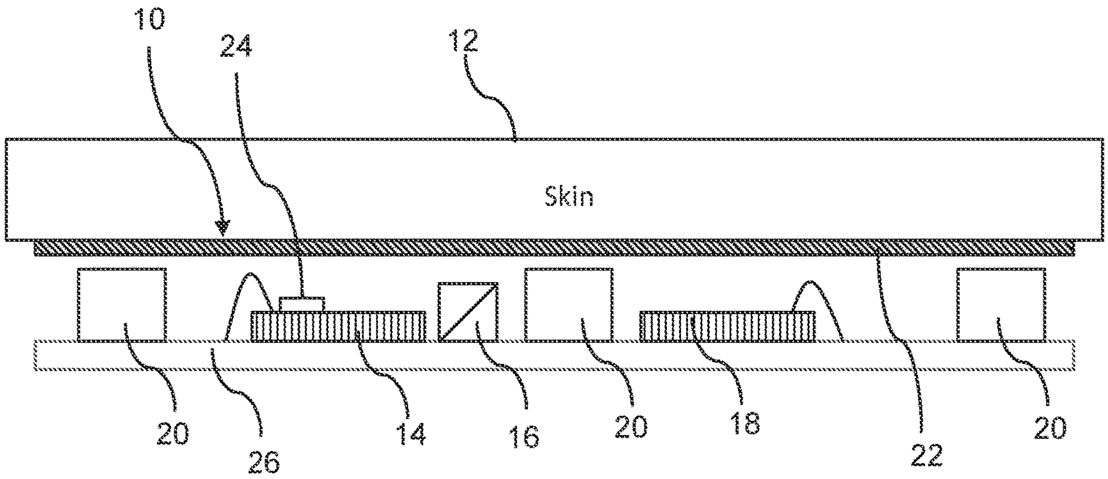
FIG. 1 shows a schematic cross-sectional view of wearable device.

A photonic integrated circuit (PIC) can comprise n lasers, such lasers optionally including ring resonator lasers, a laser generating light having a fixed wavelength and/or the laser being constructed using hybrid integration, for example with III-V RSOAs integrated into a silicon or silicon nitride photonic chip. The lasers may include a tunable laser. The PIC may have a measuring portion, an output portion, and/or a splitting/combining portion. The integer n can be greater than or equal to 2 and each laser has a laser output. However, it is also possible that one laser is provided. The measuring portion includes a measuring port and is configured to measure an intensity and/or wavelength of light input or received at the measuring port. The output portion is configured to output light form the photonic integrated circuit to the portion of the tissue. The splitting/combining portion includes n input ports, a first output port, and a second output port, wherein each input port is coupled to a respective one of the laser outputs, the first output port is coupled to the measuring port, and the second output port is coupled to the output portion. The III-V RSOAs may be made of gallium arsenide, gallium nitride and similar optical semiconductor materials.

In general, a photonic integrated circuit (PIC) can include one or more of the following features:

Visible and/or NIR (up to 1200 nm, optionally below 1000 nm) spectrometer transmitter chip (and a separate receive chip or receiver which may include a separate discreet detector or a image sensor)

Visible and NIR transmit and receive chip

One or more detectors, e.g. one or more detectors as described in PCT/IB2022/000373, the entire content of which is incorporated herein by reference N lasers Silicon nitride waveguides Ring resonator lasers (especially for $Si_4N_3$)

Hybrid integration/facet coupled

The laser being tunable

Optical Coherent detection chip

The PIC may be used in one or more of the following applications.

1) Spectroscopy
2) Improved PPG for heart rate monitor,
a. SPG (Speckle plethysmography—blood flow detection fast enough to reveal pulsatile features)
b. interferometric diffuse correlation spectroscopy (iDCS) (details of which are described in Annexes I to IV)
3) Blood oxygen measurement (optionally for N=2 or more lasers), including co-oximetry (resolving carboxyhemoglobin, methemoglobin, deoxyhemoglobin, and oxyhemoglobin)
4) Visible spectroscopy
5) NIR spectroscopy
6) Diffuse reflectance, Raman spectroscopy, Fluorescence spectroscopy, and related spectroscopies
7) Moving particles in fluids (liquids and gases)
8) Moving particles in tissue.
9) Moving particles in blood.

In an optional embodiment, the photonic integrated circuit is a silicon photonics chip. All or a majority of the optical functions necessary to generate and/or transmit optical signals and/or to receive and interpret the returning optical signals can be arranged on the silicon photonics chip.

The transmit (Tx) and receive (Rx) parts may be on one chip to form a single transmitter/receiver chip, or on more than one chip, such as a separate Tx and Rx chip device. The silicon photonics chip may be based upon an SOI structure where there is one buried oxide layer or on a double SOI structure where there are two (or more) buried oxide layers.

In an optional embodiment, the photonic integrated circuit further comprises at least one (optical) detector, wherein the photonic integrated circuit is configured to execute transmittance and/or reflectance photoplethysmography (PPG) and/or speckle photoplethysmography (SPG) measurements. In speckle plethysmography (SPG), an optical signal is used to measure changes in blood flow using laser speckle imaging or temporal decorrelation methods such as diffuse correlation spectroscopy. Laser speckle imaging may be provided on a receiver that is separate from the photonic integrated circuit.

For SPG measurements, the laser may generate light in the visible or near-infrared spectrum, for example between about 380 nm to about 850 nm, or between 380 nm to about 950/960 nm. The waveguides that are used for the SPG application can be optimized for the propagation of light in visible or near infrared spectrum or having wavelengths below 960 nm, 800 nm, or 700 nm. For example, the waveguides may be made from silicon nitride ($Si_3N_4$).

In an optional embodiment, the photonic integrated circuit is configured to execute diffuse correlation spectroscopy (DCS). DCS detects blood flow by quantifying temporal fluctuations of light fields emerging from the tissue surface. Optional embodiments are disclosed in U.S. application Ser. No. 17/814,787 and/or International Application No. PCT/EP2022/071467 which are incorporated by reference in their entirety. Optional embodiments of optical sensor modules for measuring both speckleplethysmography (SPG) and photoplethysmography (PPG) are described in U.S. application Ser. No. 17/711,974.

In an optional embodiment, the photonic integrated circuit is configured to execute diffuse reflection spectroscopy In an optional embodiment, the photonic integrated circuit executes a measurement of pulse oximetry (SpO2), oxygen saturation, carboxy haemoglobin, methaemoglobin, or fractional oxygen saturation. Optional embodiments are disclosed in WO 2021/116766 which is incorporated by reference in its entirety.

A wearable device may comprise a photonic integrated circuit as described above. The wearable device may be watch or a part of band for finger, arm, leg, and/or chest. The wearable device may provide monitoring of a pulse (heart rate), oxygen saturation, and/or parameters that are can be detected by spectroscopy of the blood in tissue.

The photonic integrated circuit may be used to determine the pulse (heart rate) of the blood flow within the tissue and/or under the tissue. The tissue may be the skin of a user of the wearable device. To this end, the user may bring the wearable device into contact with the tissue (skin) to monitor, determine, and/or record the heart rate oxygen saturation, and/or parameters that are can be detected by spectroscopy of the blood in tissue.

Various spectroscopy techniques, such as the ones described above, can be used to monitor the blood flow. These spectroscopy techniques rely on the light absorption characteristics of blood which changes depending on the oxygen saturation of the blood, such as the pulsatile oxygen saturation ($SpO_2$). These techniques may be called pulse oximetry.

To provide accurate and reliable spectroscopy measurements, such as oxygen saturation measurements, two or more lasers with wavelengths on opposite sides of an isosbestic point in the oxygen saturation curve can be used, but it can be beneficial to use various multiple wavelengths. The more wavelengths that are used for the spectroscopy measurement, the more precisely the absorption spectrum can be determined. In particular, the wavelengths generated by the n lasers can be equally distributed over parts or the complete visible spectrum and/or infrared (IR) which are commonly used to measure oxygen saturation. For example, wavelengths of 442 nm, 472 nm, 660 nm, 960 nm, and/or 1200 nm were used for determining the oxygen saturation.

One option for including more wavelengths for investigating the blood flow is to provide an array of discrete lasers each generating a light of a fixed wavelength. The lasers can be multiplexed together. This option has the disadvantage that a multitude of lasers are needed increasing the required space of the photonic integrated circuit. Alternatively, a tunable laser can be used which has the drawback that only a small wavelength range is covered by the tunable laser.

The invention provides a further optional solution, namely in that a plurality of (tunable) lasers is used for covering a wide range of different wavelengths. To this end, the wavelength range of the (tunable) lasers may not overlap with each other and/or may be equally distributed, for example over the visible and/or infrared spectrum. In particular, the wavelength ranges of the (tunable) lasers may cover those wavelength ranges that show a high absorption and, thus, increased signal to noise ratio (SNR). For example, the tunable lasers may have a centre frequency at 442 nm, 472 nm, 660 nm, 960 nm, and/or 1200 nm and a range of tunable frequencies ±10 nm, 20 nm, or 50 nm around the centre frequency. In particular, it is possible to evenly cover a wide wavelength range (for example, spanning over 100 nm, 200 nm, 500 nm, or 1000 nm) by selecting appropriate centre frequencies of the tunable lasers. Fluorescence measurements may be conducted using light of 442 nm or 472 nm. Further, blue light (e.g. 442 nm or 472 nm) may be used if the photonic integrated circuit is part of a vitro diagnostics, such as a lab-on-a-chip setup.

The visible spectrum is the portion of the electromagnetic spectrum that is visible to the human eye. Electromagnetic radiation in this range of wavelengths is called visible light or simply light. A typical human eye will respond to wavelengths from about 380 nm to about 750 nm. These wavelength boundaries are not sharply defined and may vary per individual. Under optimal conditions the limits of human perception can extend to 310 nm (UV) and 1100 nm (NIR).

Infrared (IR) light is electromagnetic radiation with wavelengths longer than those of visible light. IR is generally understood to encompass wavelengths from the nominal red edge of the visible spectrum around 700 nm to 1 mm.

The photonic integrated circuit of this invention is configured to emit the light generated by the lasers via the output portion which may have a lens or other optical component for emitting the light from the photonic integrated circuit. The light may be guided from the photonic integrated circuit through the wearable device to leave the wearable device. To this end, the wearable device may include optical components, such as waveguides, mirrors, lenses, optical filters, and/or grating which allow the light emitted by the photonic integrated circuit to be redirected, modified and/or shaped. Alternatively, the photonic integrated circuit may include all the optical functions and/or optical components such that the output portion corresponds to the output of the light from the wearable device.

The photonic integrated circuit and/or the silicon photonics chip can be located within a housing of the wearable device.

The photonic integrated circuit may include a detector for detecting the light that is reflected by and/or transmitted through that issue. The receiver or detector may be arranged on the same silicon or silicon nitride photonic chip as the lasers (the transmit chip) or on a different photonic chip. The receiver or detector may be arranged within the housing of the wearable device. There may be more than one detector on the detector chip or on the transmit/receive chip. The detector is an optical instrument that transforms light impinging onto the detector in an electrical signal. The electrical signal can be indicative of the intensity and/or wavelength of the impinging light. The detector could include multiple sensing elements such as an array or a pixelated image sensor.

Light guiding means (such as waveguides) may be provided within the wearable device for guiding the light from a light input of the wearable device do the detector. Alternatively, the detector may be located at such a position within the wearable device that light reflected and/or transmitted by the tissue and entering the variable device directly impinges on the detector without further light guiding means. However, lenses or other optical structures for focusing and/or collecting the light reflected and/or transmitted by the tissue may be provided. Further, lenses or other optical structures for focusing the light generated by the lasers onto the issue may be provided.

The lasers, the measuring portion, the output portion, and/or the splitting/combining portion are coupled or connected to each other to allow transmission of light between these components. To this end, these components may be coupled or connected to each other via one or more optical waveguides or other types of optical components allowing the transmission of light. The optical waveguides may be part of the optical photonics chip. Thus, it is possible that light can be guided from one of these components to another one of these components. The optical waveguides may be configured to transmit radiation in the visible spectrum and/or MR (up to 1200 nm, optionally below 1000 nm). For example, the waveguides are made from silicon nitride.

It is also possible that a free space (filled with air) is arranged between the lasers, the measuring portion, the output portion, and/or the splitting/combining portion such that light can travel through the free space from one of these components to another one of these components.

The laser output may be that part of the (tunable) laser where the light generated by the (tunable) laser exits the (tunable) laser. For example, the laser output may be coupled or connected to a waveguide or corresponds to a section/end of a waveguide of the (tunable) laser. The (tunable) laser may be configured to generate light of discrete wavelengths or to cover a continuous wavelength range. The light emitted by the (tunable) laser has a certain wavelength and/or an intensity which can be set using a control portion controlling the (tunable) laser. There are n laser outputs as each laser includes a laser output.

The measuring portion is configured to measure the intensity and/or the wavelength of light received or input at the measuring port. The measuring port may be considered an input port of the measuring portion, i.e. a part of the measuring portion configured to receive light. For example, the measuring port is connected to a waveguide.

Optionally, the measuring portion includes a wavemeter for determining the wavelength of the light input at the measuring port and/or a photodetector for measuring the intensity of the light input at the measuring port. A wavemeter (or wavelength meter) can be a kind of interferometer which is used for precise wavelength measurements for light. There are different variants, including scanning wavemeters and static devices with no moving parts.

The wavemeter transforms the light impinging onto the wavemeter into an electrical signal. The electrical signal can be indicative of the wavelength of the impinging light.

The photodetector is an optical instrument that transforms light impinging onto the photodetector into an electrical signal. The electrical signal can be indicative of the intensity of the impinging light.

In case the measuring port includes both the wavemeter and the photodetector, the measuring port includes an optical splitter which is connected to the measuring port and splits the incoming light to the wavemeter and the photodetector. The measuring portion may include one or more optical waveguides for guiding the light from the measuring port to the splitter and/or from the splitter to the wavemeter and the photodetector.

The output portion may include one or more optical waveguides and/or one or more lens structures which allow the emission of the light generated by the (tunable) lasers from the photonic integrated circuit. This light may be directly emitted from the wearable device or the light emitted from the output portion may be guided through the wearable device to an output of the wearable device. The waveguides of the output potion may end at an edge of the photonic integrated circuit and can include the lens structure at their end. For example, each waveguide has a separate lens structure or there is a common lens structure coupled to the waveguides. It is also possible that there is no lens structure such that a distal end surface of the waveguides provides the point at which the light is emitted from the photonic integrated circuit.

The output portion may include one or more output ports configured to receive light from the splitting/combining portion. One or more waveguides of the output portion are coupled to the output port. For example, each waveguide of the output portion has an output port connected to a respective second output port of the splitting/combining portion or waveguides connecting the output ports and the second output ports.

The splitting/combining portion is provided for distributing the light generated by the (tunable) lasers to the measuring portion and the output portion. In detail, the splitting/combining portion includes n input ports each of which is coupled to a respective one of the n (tunable) lasers—each input port is coupled to a respective laser output, for example by a waveguide. The input ports are configured to receive light generated by their respective (tunable) lasers. This means, at each input port, light of a different (tunable) laser is received.

The first output port is coupled to the measuring portion, for example by a waveguide. The number of the first output ports depends on the way how the splitting/combining portion combines/splits the light received at the input ports. The second output port is coupled to the output portion, for example by a waveguide. The number of the second output ports depends on the way how the splitting/combining portion combines/splits the light received at the input ports. However, the number of second output ports corresponds to the number of output ports.

In an optional embodiment, the splitting/combining portion includes n optical splitters, wherein optionally each optical splitter is coupled to one input port, one first output port, and one second output port.

In an optional embodiment, the optical splitter includes a directional coupler, Y-branch coupler and/or a multimode interference splitter (MMI splitter). The optical splitter may be considered a (power) tap.

In this embodiment, each (tunable) laser is coupled to a single optical splitter which splits the light generated by each (tunable) laser to the measuring portion and the output portion. This means that the intensity and/or wavelength of each (tunable) laser is monitored, and the light generated by each (tunable) laser is output at the output portion.

In an optional embodiment, the output portion includes n output channels, each output channel being coupled to one second output port.

The output channel may include a waveguide such that, in this configuration, the output portion includes n separate waveguides. Each output channel or waveguide is optically coupled to the optical splitter via a respective second output port and a respective output port. Thus, there are n output ports and n second output ports which can be connected by n waveguides.

This allows a segmented configuration of the photonic integrated circuit whereby each segment of the photonic integrated circuit includes a single (tunable) laser, single optical splitter, a single wavemeter and/or single optical detector, and single output channel. Thus, the photonic integrated circuit includes n segments. This may be considered a first embodiment of the architecture of the photonic integrated circuit.

In an optional embodiment, the splitting/combining portion includes one optical combiner and one optical splitter, wherein optionally the optical combiner is coupled to the n input ports for combining the light of the n lasers, the optical splitter is coupled to the optical combiner, to the first input port, and the second input port for splitting the light received from the optical combiner into the first output port and the second output port.

In an optional embodiment, the output portion includes one output channel that is coupled to the optical splitter.

In an optional embodiment, the optical combiner includes an optical multiplexer (MUX). The optical multiplexer may take the form of an echelle grating, specifically an integrated echelle grating, or an arrayed waveguide grating (AWG).

In this embodiment, the optical multiplexer combines the light generated by the n (tunable) lasers. Input ports of the optical multiplexer can be considered the input ports of the measuring portion. This means that the optical multiplexer has n input ports which are respectively coupled to the n laser outputs, for example via n waveguides.

The optical multiplexer is coupled to the optical splitter, for example via a single waveguide. This means that the optical multiplexer can include a single output port connected to the waveguide. The optical splitter splits the multiplexed light into the measuring portion and the output portion. In this case, the output portion may include one optical channel or one waveguide. Further, only a single optical splitter, a single wavemeter, and/or a single photodetector are provided.

This embodiment allows the reduction of the number of components, since only one optical splitter, one output channel, one wavemeter, and/or one photodetector are provided. Thus, the photonic integrated circuit requires less space compared to the previous embodiment. This may be considered a second embodiment of the architecture of the photonic integrated circuit.

In an optional embodiment, the splitting/combining portion includes n optical splitters and one optical combiner, wherein optionally each optical splitter is coupled to one input port, to the one optical combiner and to the second output port for splitting the light received from the respective (tunable) laser into the optical combiner and the second output port, and wherein further optionally the optical combiner is coupled to the measuring portion for combining the light received from the n optical splitters.

In an optional embodiment, the output portion includes n output channels, each output channel being coupled to a respective one of the optical splitters.

Optionally, each input port of the n input ports of the splitting/combining portion is coupled to a respective splitter, for example via a waveguide. Thus, there may be n waveguides for the n optical splitters. Alternatively, the n input ports of the splitting/combining portion are the input ports of the n optical splitters. As a consequence, n first output ports and a second output ports are provided. Each first output port and each second output port may be coupled to the respective optical splitter via a waveguide resulting in 2 n waveguides. Alternatively, the n first and second output ports of the splitting/combining portion are the first and second output ports, respectively, of the n optical splitters.

The n first output ports are coupled to the optical multiplexer, for example via n waveguides. The optical multiplexer combines the light generated by the n (tunable) lasers and forwards the light to the measuring portion. The measuring portion may include a single wavemeter and/or single photodetector.

This may be considered a second embodiment of the architecture of the photonic integrated circuit. In this embodiment, the intensity and/or wavelength of each of the n (tunable) lasers is measured using a single wavemeter and/or single photodetector while each (tunable) laser has a separate output, i.e. a separate output channel. Thus, the optical multiplexer does not affect the light that is emitted from the photonic integrated circuit. The light output by the photonic integrated circuit does not suffer from optical losses due to the optical multiplexer. In addition, the number of components can be reduced compared to the first embodiment.

In an optional embodiment, the photonic integrated circuit further comprises a control portion coupled to the n tunable lasers and configured to tune the n tunable lasers. Optionally, the control portion is coupled the measuring portion and configured to tune the n tunable lasers based on the intensity and/or the wavelength measured by the measuring portion.

In an optional embodiment, the control portion tunes all n tunable lasers using a common tuning parameter.

The control portion may be an electrical component including a processor and/or memory providing electrical control of the (tunable) laser. The control portion may be located external to the silicon photonics chip or on the silicon photonics chip. The control portion may be arranged within the housing of the wearable device. The control portion can be configured to tune the wavelength and/or the intensity of the light that is generated by the (tunable) lasers. To this end, the control portion may output an electrical signal to the tunable laser based on which the tunable laser changes the wavelength and/or the intensity of the generated light. For example, a change in a tuning parameter of the electrical signal (such as voltage, frequency and/or current) results in a change in the wavelength and/or the intensity of the generated light.

The control portion may be configured to separately control each of the n (tunable) lasers. Thus, the control portion outputs n electrical signals or n tuning parameter. Alternatively, the control portion outputs a single electrical signal that is received by all n (tunable) lasers. Thus, the control portion outputs a single electrical signal or a single tuning parameter.

If the control portion is electrically connected to the measuring portion, a feedback control of the wavelength and/or the intensity of the light generated by the (tunable) lasers can be established. Alternatively, the control portion may control the (tunable) lasers independent from the measuring results of the measuring portion.

In an optional embodiment, the output portion includes an optical mode mixing device and/or beam steering device for mitigating speckle. The mixing device and/or the beam steering device are located on the silicon photonics chip and/or are provided for reducing speckle of laser beam(s) emitted by the photonic integrated circuit. For example, each output channel of the output portion may include a separate mixing device and/or the beam steering. Optional details on the output portion and/or optional embodiments of the output portion are described in Annexes I and II.

In an optional embodiment, each tunable laser includes a reflective semiconductor optical amplifier (RSOA) and a tuning element, wherein optionally the tuning element includes a micro-ring reflector and/or a sampled Distributed Bragg Reflector (DBR) grating.

The tunable laser may include a heater for heating the tuning element resulting in a change of the wavelength emitted by the tunable laser. The tuning parameter may be a voltage, current and/or power that is output to the heater resulting in a different temperature of the tuning element which in turn results in different wavelength. Thus, the heater may heat parts of the micro-ring reflector and/or a sampled Distributed Bragg Reflector.

The tuning element may be used to tune/change/alter the wavelength of the light emitted by the RSOA. The tunable laser may include a photodiode for generating light of a particular frequency that is amplified by the RSOA. Thus, control of the photodiode for generating light may be used for varying the intensity of the light generated by the tunable laser. For example, the tuning parameter may be a voltage, current and/or power that is output to the photodiode resulting in a different intensity of the generated light.

In an optional embodiment, at least one of the n tunable lasers includes phase control section coupled between the reflective semiconductor optical amplifier (RSOA) and the tuning element for determining the phase of light.

The RSOA may be coupled to the tuneable element by a waveguide which is coupled to the phase control section. The phase control section may include one or more optical elements allowing the detection of the phase of the light propagating in the waveguide between the tuneable element and the RSOA. The phase control section may be electrically connected to the control portion such that the phase of the light may be a control parameter for controlling the light.

In an optional embodiment, a Fabry-Perot laser is provided. This Fabry-Perot laser may be provided for diagnostic purposes and/or test purposes, but is not essential for the overall function of the photonic integrated circuit. The Fabry-Perot laser circuit may include a separate photodiode for generating light and the RSOA. The Fabry-Perot laser maybe coupled to an output for emitting the generated light from the photonic integrated circuit independent from the output portion.

In an optional embodiment, the photonic integrated circuit includes more than one of the embodiments described above, for example a combination of the first, second, and/or third embodiment. This means that a part of the (tunable) lasers provided on the photonic integrated circuit are coupled to each other according to one of the embodiments described above, while other (tunable) lasers are coupled to each other according to another embodiment described above. For example, the photonic integrated circuit includes a+b=n lasers (a & b being integers greater than or equal to 2), wherein a (tunable) lasers are coupled to each other according to the first embodiment and b (tunable) lasers are coupled to each other according to the second or third embodiment.

A method for controlling a photonic integrated circuit (PIC) comprises a) setting a tuning element of a laser, b) turning the laser on for generating laser light having a wavelength and an intensity, c) measuring the intensity and/or the wavelength of generated laser light, and d) detecting the reflection of the generated laser light from the portion of the tissue and analysing the reflected light for investigating the blood flow, volume, or other chromophore wherein optionally the laser includes a ring resonator laser, a laser being constructed using hybrid integration, and/or a tunable laser.

A method for controlling a photonic integrated circuit for optically investigating blood flow at a portion of tissue of a user comprises a) setting a tuning element of one of n tunable lasers, n being an integer greater than or equal to 2, b) turning the one of the n tunable lasers on for generating laser light having a wavelength and an intensity, c) measuring the intensity and/or the wavelength of generated laser light, d) detecting the reflection of the generated laser light from the portion of the tissue and analysing the reflected light for investigating the blood flow, volume, or other chromophore and e) repeating steps a) to d).

The method may be executed by the control portion. Thus, the method may be a (computer-implemented) method for controlling the photonic integrated circuit described above.

Step a) refers to setting or tuning the wavelength of the light generated by one or more/all of the tunable lasers. To this end, the control portion may output an electrical signal having a certain tuning parameter or change the tuning parameter of the electrical signal.

Step a) may be executed before step b). This means that the tuning element is set or tuned before light is generated by the photodiode/RSOA. However, step b) can be executed before step a).

Step b) may also include setting the intensity of the light generated by one or more/all of the (tunable) lasers. This is also done by starting the output of the electrical signal or by changing a tuning parameter of the electrical signal to the (tunable) laser (in particular the photodiode). The intensity and/or the wavelength generated by the photodiode/RSOA may be different to the intensity and/or the wavelength by the (tunable) laser since the tuning element changes the wavelength and potentially the intensity.

Step c) refers to measuring the intensity and/or the wavelength that is emitted by the (tunable) laser, i.e. the light that is modified by the tuning element. Step c) may be executed by the measuring portion.

Step d) may be executed by the detector and can be executed simultaneously to step c). Thus, feedback control of the generated laser light and detection of the light reflected and/or transmitted by the tissue can be simultaneously done. Step c) includes processing the detected light in order to determine the blood flow. This may be done by the control portion or by a processor external to silicon photonics chip. This processing is known in the field and, thus, not further described here.

Step e) refers to the repetition of steps a) to d) such that each wavelength that is generated by the different photodiodes/RSOAs and each tuned wavelength is used for determining the blood flow. This can be done by scanning firstly to all the wavelengths that can be tuned by the respective tuning element of a tunable laser and then repeating this process for each tunable laser. Alternatively, a particular tunable laser with a particular tuning setting is measured and, in the next step, another tuneable laser is turned on with a particular tuning setting. This step is repeated until all tunable lasers have been turn on and off. Then, the tuning parameter is changed, and the above cycle is repeated for each of the different tuning parameters. Thus, step e) includes varying the tunable lasers and varying the tuning of each of the tunable lasers. After completion of the method, a wide range of different wavelengths has been used for determining the blood flow, volume, or other chromophore increasing the reliability and accuracy of the measurement of the blood flow, volume, or other chromophore. Optionally, all wavelengths that can be generated by the n tunable lasers are used in the method.

In an optional embodiment, step a) is executed based on pre-calibrated set points and, optionally, before step b).

This embodiment may include setting the tuning parameters independent of the measurements result received in step c), i.e. no feedback control of the (tunable) laser is used. The accuracy of the (tunable) lasers may be achieved by calibrating the photonics integrated circuit and the tuning parameters refer to pre-calibrated values.

The execution of step a) before step b) may allow the tuning elements to settle resulting in a more reliable tuning of the wavelength.

In an optional embodiment, step e) is repeated for each one of the n tunable lasers and each wavelength that can be generated by the n tunable lasers. In particular, all wavelengths that can be tuned with a particular tunable laser are scanned through before switching to another tunable laser.

In an optional embodiment, step a) includes simultaneously setting the tuning elements of all n tunable lasers and wherein step e) includes repeating steps b) to d) for each one of the n tunable lasers before returning to step a).

In this embodiment, all n tunable lasers are controlled by the same tuning parameter regarding the tuning element. A certain tuning parameter is output to all n tuning elements. Then, generation of light of a certain tunable laser is started and the response of the blood flow detected. Afterwards, the generation of light of this tunable laser is stopped and different tuneable laser is turned on. If all n tunable lasers were turned on and off again for the respective blood flow measurement, a new tuning parameter for the tuning elements is output and the above-described cycle is repeated.

In an optional embodiment, step b) is executed before a), wherein optionally the setting of the tuning element of the one of the n tunable lasers is based on the results achieved in step c).

This allows an optimization of the tuned wavelength based on the wavelength detected by the measuring portion. In this case, step c) may include a sub step of optimising the wavelength generated by the tunable laser before the actual measurement of the blood flow is executed.

In an optional embodiment, steps a) to d) define a first cycle which includes varying the setting of the tuning element for the one of the n tuning elements and a second cycle of repeating the first cycle which includes changing the one of the n tunable lasers.

In this embodiment, all wavelengths that can be generated by a particular wavelength are measured before switching to a different tunable laser.

In an optional embodiment, wherein steps c) and d) are simultaneously executed. This allows a calibration/adaption of the blood flow measurements depending on variations in the intensity and/or wavelength of the light emitted to the tissue.

An optical coupler may comprise a first optical element including a first waveguide and a second optical element including a second waveguide and an end portion. The first waveguide includes a facet configured to emit electromagnetic radiation from the first optical element. The end portion is configured to couple electromagnetic radiation into the second optical element. The first optical element and a second optical element are fixed so that the facet faces the end portion. The end portion includes a plurality of nanobeams wherein each nanobeam has a width that is smaller than the width of the second waveguide. The end portion includes a merging section at which the nanobeams merge. The optical element further includes a tapered portion arranged between the merging section and the second waveguide. A minimal width of the merging section is smaller than the width of the second waveguide.

The nanobeams may have a dimension (e.g. width and/or height) between 300 nm and 50 nm, optionally 200 nm or less, 150 nm or less, 100 nm or less. The nanobeam may be considered a nano-waveguide.

Waveguides are basic elements of optical systems that can carry light between different sections of a photonic chip. However, photonic chips are usually not uniform on a single aperture substrate, mainly due to the fabrication incompatibility between active and passive materials. Therefore, transferring light from one part of the photonic chip to another part of the photonic chip in an efficient way is required. So far, various methods have been studied for coupling light from a fiber optic structure to an integrated optical waveguide using grating, inverse taper design, end couplers, and lateral couplers. In all these proposals, the main objective is to design an intermediate transition part between two different waveguides that can smoothly transfer light by matching the mode sizes and effective refractive index values.

While some techniques can achieve high coupling efficiencies, but mainly they rely on bulky components such as micro positioners to precisely control the angle and distance of two waveguide structures. Therefore, they are barely compatible for real applications and packaging in nano scales unless with poor coupling efficiencies. For example, coupling from an RSOA chip to a passive integrated waveguide (e.g., silicon-based) is crucial because active materials are not compatible with complementary metal-oxide-semiconductors (CMOS). Therefore, the output light from an RSOA needs to be coupled to a PIC externally.

There are two common approaches to couple light from an active device into a PIC: (1) lateral coupling from top side of chip and using evanescent waves, (2) end coupling from the edge of chip. Both methods may use bonding for practical applications. The focus of this embodiment is on the second approach.

The optical coupler may be used with the photonic integrated circuit (PIC) described above. For example, the first optical element can be the RSOA and the second optical element may be the tunable filter. In other words, the optical coupler can be used with the tunable laser described above.

The first optical element may be manufactured on a first substrate while the second optical element may be manufactured on a second substrate so that the first optical element and the second optical element may need to be assembled for providing the optical coupler (e.g. the tunable laser). For example, the first optical element is fixed to the second act optical element by using an adhesive such as a glue. However, any means for fixing the first optical element with respect to the second optical element are possible as long as there is a fixed relationship between the first optical element and the second optical element.

The first waveguide and/or the second waveguide may be waveguides as described above, i.e. optical structures for conveying electromagnetic radiation. For example, the first optical element includes a light source which generates electromagnetic radiation such as monochromatic light. The electromagnetic radiation generated by the light source (e.g. a RSOA as described above) is conveyed by the first waveguide to the facet.

The facet may be an end surface of the first optical waveguide from which the electromechanical radiation conveyed in the first waveguide is emitted from the first optical element. The facet may be close to or flush with a side surface of the first substrate of the first optical element. This means that the facet is arranged close to or at an edge of the first substrate.

Similarly, the end portion may include several end surfaces for each nanobeam so that light can be coupled into the respective nanobeams via these end surfaces. In other words, the end portions may include facets, i.e. each nanobeam includes a facet which faces the facet of the first waveguide. The end surfaces or facets of the nanobeams may be arranged in a single plane which might be close to or flush with a side surface of the first substrate of the first optical element. This means that the facets or end surfaces of the nanobeams are arranged close to or at an edge of the second substrate.

The nanobeams and the merging section may form a fork shape. The nanobeams are the prongs of the fork while the merging section is the portion of the fork to which each nanobeam is connected. So the nanobeams are in optical communication with the merging section which is in optical communication with the tapered portion. The nanobeams may have a width which is smaller than the width of the second waveguide for example less than 10%, 15%, 20%, or 25% of the width of the second waveguide. The maximal distance between the respective nanobeams may be more than the width of the nanobeams.

Optionally, there is an odd number of nanobeams. For example, there is a center nanobeam which is in the middle of a pair of nanobeams. One, two, or more pairs of nanobeams may be provided whereby the first nanobeam is arranged between the second pair of nanobeams, etc. Each pair of nanobeams may form a Y-coupler at the merging section.

The tapered portion is in optical communication with the merging section and the second waveguide so that there is an optical pathway from each facet of the respective nanobeam to the merging section via the tapered portion to the second waveguide. The end portion (e.g. all nanobeams), the tapered portion, the merging section and/or the second waveguide may be a unitary component. The second waveguide may be in optical communication with other optical components (e.g. the above-described measuring portion and/or the above-described port) arranged on the second optical element.

The tapered portion may have a minimal width which less than the width of the second waveguide, for example less than 10%, 15%, 20%, 25%, 30%, 40%, or 50%. Optionally, the tapered portion has the same width as the width of the nanobeams. The second waveguide may be configured for multimode propagation of light. This means that a width and a height of the second waveguide are chosen such that multiple modes of electromagnetic radiation can propagate within the second waveguide. In contrast thereto, the tapered portion may have a width and height which are chosen should such that only a single mode of electromagnetic radiation can propagate within the tapered portion. The tapered portion may act as a multimode filter allowing only the propagation of a single mode.

The facets of the nanobeams facing the facet of the first waveguide may be spaced apart along the side surface of the second optical element which can be positioned opposite to the facet of the first waveguide. The fixation of the first optical element to the second optical element may not be done with such accuracy that an offset of the first waveguide with regard to the second waveguide can be avoided. The provision of the plurality of nanobeams is immune to a slight offset of the first waveguide with respect to the second waveguide (or the plurality of nanobeams). A width of the assembly of the plurality of nanobeams can be chosen such that it is larger than an accuracy of the fixation of the first waveguide with respect to the second waveguide. This means that, if the first optical component is fixed to the second optical component within the accuracy range, the electromagnetic radiation emitted by the first waveguide is reliably coupled into one or more of the nanobeams. In particular, the electromagnetic radiation emitted by the first waveguide propagates simultaneously in or more of the nanobeams. The intensity of the electromagnetic radiation in the respective nanobeam depends on its proximity to the facet of the first waveguide, i.e. on the unique fixation of the first optical component with respect to the second optical component. Since the width of the assembly of the plurality of nanobeams is chosen greater than the accuracy of the fixation of the first optical element to the second optical element, light can be reliable coupled into the second optical component since one or more of the nanobeams is sufficiently close to the facet of the first waveguide. For example, a coupling tolerance of 0.5 dB drop in maximum efficiency against lateral misalignment is ±0.5 μm.

The optical coupler is not only less susceptible to manufacturing inaccuracies but also exhibits a coupling loss which can be as low as −1 dB. Further, a wavelength bandwidth of 0.5 dB drop in maximum efficiency can be about 300 nm with a center wavelength of 950 nm.

In an optional embodiment, the width of each of the nanobeams is constant and/or respective sections of the plurality of the nanobeams extend parallel to each other.

The nanobeams may include a straight section and a curved section. The straight section of each nanobeam extends parallel to the straight sections of the other nanobeams. The straight section may include the facet of the nanobeam. The curved section is provided for guiding the respective straight sections to the merging section. The straight section and the curves may have the same width.

In an optional embodiment, a first angle between the direction of extension of the first waveguide and a plane of the facet is between 80° and 84°, optionally 82°.

This means that the facet is inclined (i.e. not perpendicular) to the direction of extension of the first waveguide close to the facet. This improves the out-coupling characteristics of the first waveguide. For example, less light is reflected back into the first waveguide at the facet. The facet may be flush with a side surface of the substrate of the first optical element. This means that the side surface of the first optical element is inclined (i.e. not perpendicular) to the direction of extension of the first waveguide close to the facet, for example by 80° and 84°, optionally 82°. The back-reflection at the facet can be less than 0.1%.

In an optional embodiment, a side surface of the second optical element extends parallel to the facet, wherein optionally a second angle between the direction of extension of the parallel sections of the plurality of nanobeams and a plane of the side surfaces between 79° and 83°, optionally 81°.

The facets of the nanobeams may be arranged parallel to the facet of the first waveguide. The straight sections of the nanobeams and/or the second waveguide may extend perpendicular to the side surface of the second optical component—this means perpendicular to the facet of the first optical element. However, it is also possible that the side surface of the second optical component and the straight sections of the nanobeams and/or the second waveguide to define an angle less than 90° (the second angle). The second angle is provided to accommodate a further diffraction of the light by the adhesive between the first optical element and the second optical element. For example, the adhesive diffracts the electromagnetic radiation by 9°. This is addressed by selecting an second angle of 81° between the straight sections of the nanobeams and the side surface of the substrate of the second optical element.

In an optional embodiment, the end portion is spaced apart from the side surface, wherein optionally a space between the side surface and the end portion is filled with silicon dioxide ($SiO_2$).

In this embodiment, the facets of the nanobeams are spaced apart from side surface of the second optical element and/or an edge of the substrate of the second optical element. This space is filled with a material such as silicon dioxide. This means that a side surface of the second optical element is defined by this material.

In an optional embodiment, the first waveguide includes a T-bar providing facet.

The T-bar may be constituted by an end section of the first waveguide. The end section can be formed so that the end section and the facet provided thereon have a width greater than a width of the first waveguide leading to the end section. Optionally, the end section and/or the facet have a width of least W+2R, wherein W is the width of the first waveguide leading to the end section and R is the radius of curvature of corners of the end section caused as a result of the manufacturing process used to fabricate the end section or T-bar. This may ensure that an area of the facet at which the electromagnetic radiation exits the first waveguide is planar, i.e., free from curvatures or round corners that may result in back reflection of the electromagnetic radiation at the facet. Thus, the T-bar can help to prevent back reflection at the facet. The T-bar may have a height that is equal to the height of the first waveguide. Optionally, a side surface of the T-bar corresponds to the facet of the waveguide.

FIG. 1 shows a wearable device 10 in contact with skin 12 which is an example of a portion of a tissue in which a blood flow is investigated. The wearable device 10 may be a part of a watch or wristband.

The wearable device 10 includes a silicon photonics chip 14, a mirror 16, a light detector 18, optical barriers 20, and/or a glass 22. The silicon photonics chip 14 may include electrical circuitry, such as a control component 24, and a photonic integrated circuit (PIC) 28 which is not visible in FIG. 1. The control component 24 controls the photonic integrated circuit which generates laser light that is directed to the mirror 16. The mirror 16 reflects the light through the glass 22 towards the skin 12. The light generated by the photonic integrated circuit is reflected by the blood within the skin, transmitted by the glass 22, and received by the light detector 22. The light detector 22 may include any sensor which is configured to transform the received light into an electrical signal, whereby the electrical signal may vary depending on the wavelength and/or intensity of the received light. The electric signal generated by the light detector 22 can be forwarded to the control component 24 or another processor not shown in the figures for analysing the received light in order to determine or investigate the blood flow in the skin 12.

The light barriers 20 may be made from optically opaque material in order to separate the generation of light from the detection of the reflected light. The wearable device 10 may include a printed circuit board (PCB) 26 on which the silicon photonics chip 14, the mirror 16, the light detector 18, and/or the optical barriers 20 are arranged. The printed circuit board (PCB) 26 may include the processing means for analysing the light received by the light detector 18. The wearable device 10 may include further components which are not depicted in the figures. The printed circuit board 26 may also be configured to execute the functions of the control portion 24.

Figure 2:
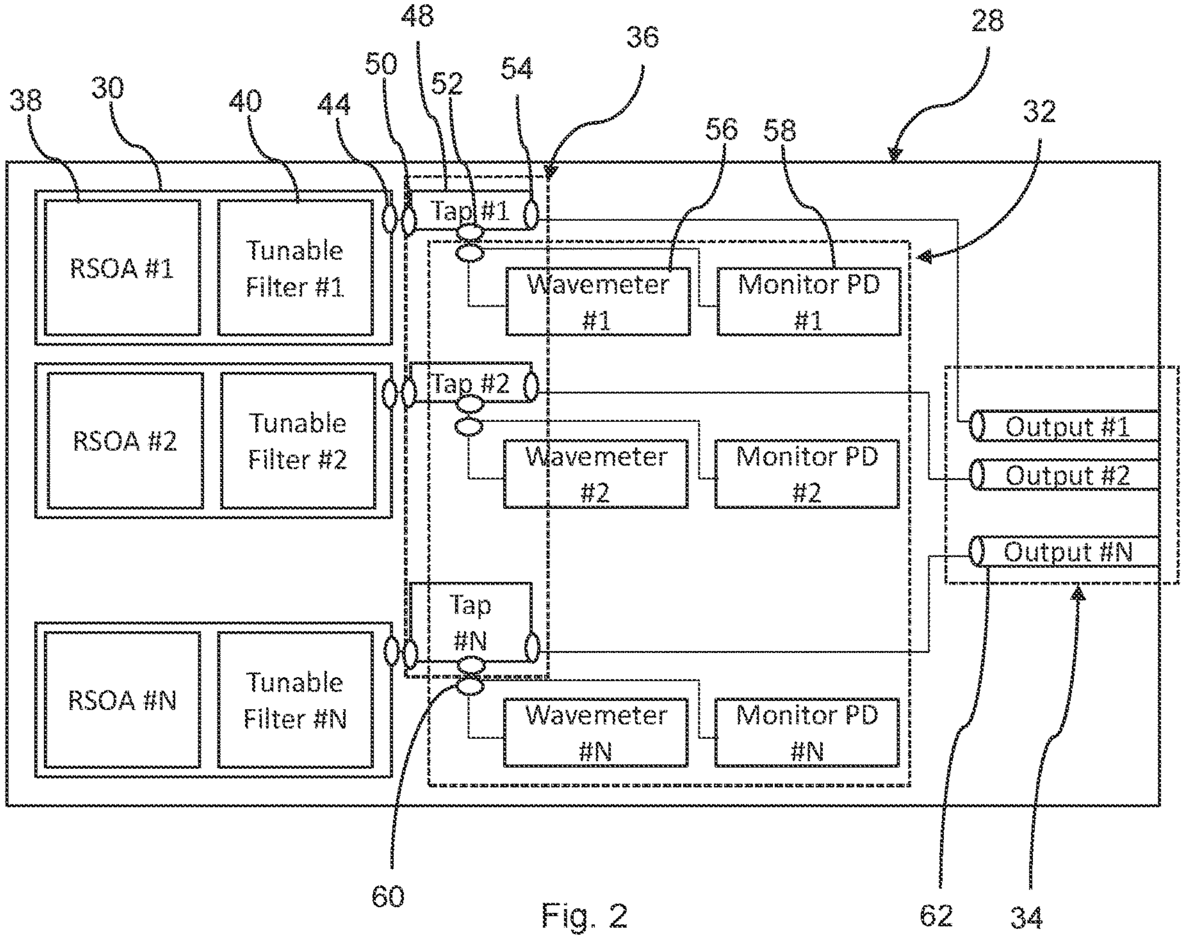
FIG. 2 shows a block diagram of the components of a first embodiment of a photonic integrated circuit arranged in the wearable device.

One embodiment of the architecture of PIC 28 is depicted in FIG. 2. The PIC 28 includes n tunable lasers 30, a measuring portion 32, an output portion 34, and splitting/combining portion 36. Each of the tunable lasers 30 are electrically connected to the control portion 24. The tunable lasers 30 can generate light having an intensity and a wavelength, whereby the wavelength can be tuned based on an electrical signal defining a tuning parameter and generated by the control portion 24. Thus, each tunable laser 30 may provide light having different wavelengths, for example a plurality of discrete wavelengths. For example, 2, 4, or 10 tuneable lasers may be provided—in general n is an integer greater or equal to 2.

Each tunable laser 30 may include a reflective semiconductor optical amplifier (RSOA) 38 and a tuning element 40 (indicated as "Tunable Filter #N" in FIG. 2). The RSOA 38 maybe coupled to a photodiode 39 for generating light that is amplified by the RSOA 38 (see FIG. 5). The tuning element 40 may include a micro-ring reflector 42 (see FIG. 5) and/or a sampled Distributed Bragg Reflector (DBR) grating. Further, the tuning element 40 may include heater (not shown in the figures) for heating the tuning element 40. The wavelength generated by the tunable laser 30 varies depending on the temperature of the tuning element 40. Thus, the voltage, current, and/or power supplies to the heater may be considered a tuning parameter. Thus, the control portion 24 can change the wavelength of the tunable laser 30 by changing the temperature of the heater.

The tunable laser 30 may further include a laser output 44 at which the light generated by the tunable laser 30 exits the tunable laser 30. For example, the laser output 44 is coupled to a waveguide which transmits the light generated by the tunable laser 30 to the splitting/combining portion 36.

The measuring portion 32 may include one or more optical combiner 46 and/or one more optical splitters 48. The optical splitter 48 includes a directional coupler (see FIG. 5) and/or a multimode interference splitter. The optical combiner 46 includes an optical multiplexer.

In the embodiment depicted in FIG. 2, the splitting/combining portion 36 includes n optical splitters 48 (indicated as "Tap #N" in FIG. 2), but no optical combiners 46. Each optical splitter 48 includes an input port 50, a first output port 52, and a second output port 54. Thus, the splitting/combining portion 36 includes n input ports 50, n first output ports 52, and n second output ports 54.

The input port 50 is optically coupled to the laser output 44 (e.g. via a waveguide) for receiving light from a respective tunable laser 30; the optical splitter 48 #1 receives light from tunable laser 30 #1, the optical splitter 48 #2 receive light from tunable laser 30 #2, etc. The first output port 52 is optically coupled to a measuring port 60 of the measuring portion 32 (e.g. via a waveguide) for receiving light from a respective optical splitter 48. The second output port 54 is optically coupled to the output portion 34. Thus, the splitting/combining portion 36 distributes the light generated by the tunable lasers 30 to the measuring portion 32 and the output portion 34.

The measuring portion 32 may include a wavemeter 56 for determining the wavelength of the light input at a measuring port 60 and/or a photodetector 58 (indicated as "Monitor PD #N" in FIG. 2) for measuring the intensity of the light input at the measuring port 60. The measuring portion 32 may further an optical splitter coupled to the measuring port 60. The measuring port 60 is optically coupled to the splitting/combining portion 36—in particular to the first output port 50—for receiving light from the splitting/combining portion 36. The light received at the measuring port 60 is split by the optical splitter into the wavemeter 56 and the photodetector 58. The wavemeter 56 and the photodetector 58 may be electrically connected to the control portion 24.

The output portion 34 is that part of the PIC 28 at which the light is emitted from the PIC 28. For example, the output portion 34 directs the light to the mirror 16. The output portion 34 includes, in the embodiment of FIG. 2, n output channels 62 (indicated as "Output #N" in FIG. 2) which each may be implemented by an optical waveguide. Each output channel 64 may be optically coupled to the second output port 52, for example via an optical waveguide. Thus, each output channel 62 is optically coupled to a respective optical splitter 48.

In the embodiment of FIG. 2, each optical splitter 48 splits the light of a respective tunable laser 30 into a respective combination of wavemeter 56 and photodetector 58 and the respective output channel 62. Thus, the embodiment of FIG. 2 may be considered a segmented architecture in that the light generated by each tunable laser 30 is split by a respective optical splitter 48 into a respective wavemeter 56/photodetector 58 one the one hand and into a respective output channel 62 on the other hand.

Figure 3:
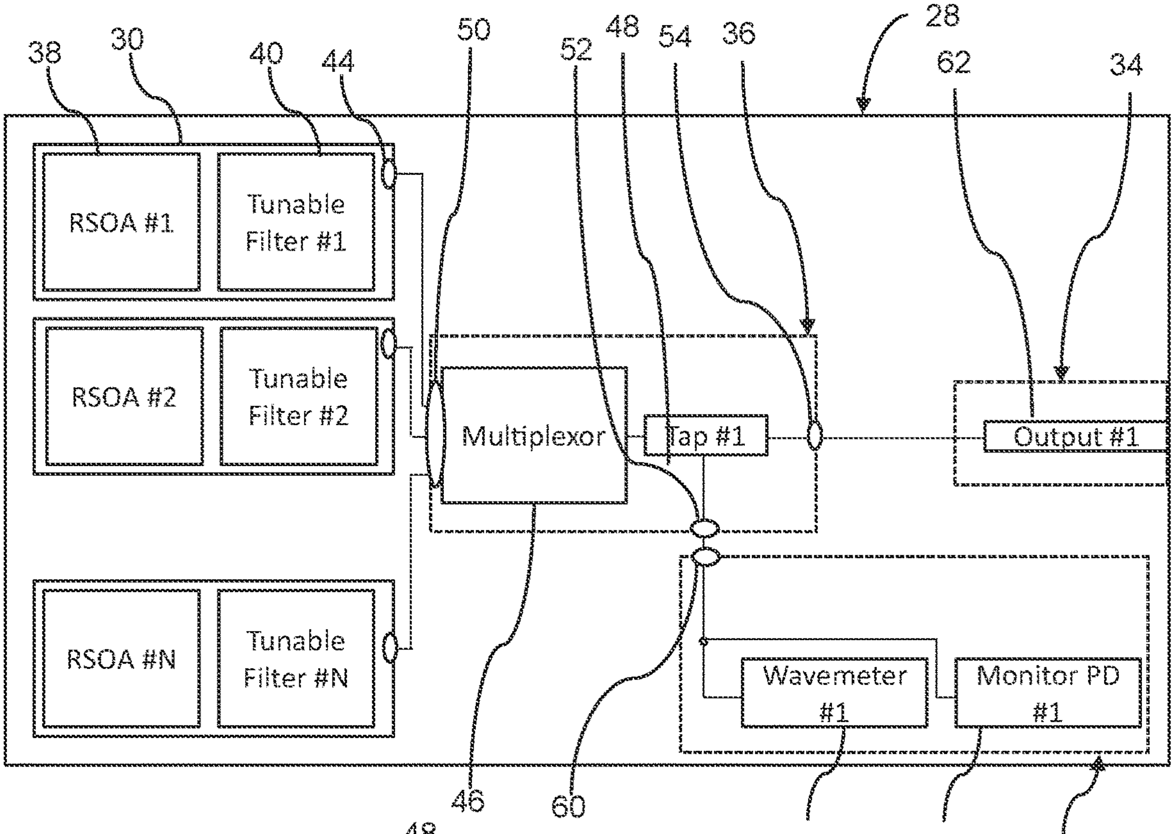
FIG. 3 shows a block diagram of the components of a second embodiment of the photonic integrated circuit arranged in the wearable device.

The embodiment depicted in FIG. 3 has the same configuration as the embodiment depicted in FIG. 2 except for the following differences.

The splitting/combining portion 36 includes a single optical combiner 46 and a single optical splitter 48. The measuring portion 32 includes a single wavemeter 56 and a single photodetector 58. The output portion 34 includes a single output channel 62.

The optical combiner 46 is a multiplexer which combines the light generated by each of the tunable lasers 30. The optical combiner is optically coupled to the optical splitter 48 which splits the multiplexed light into the measuring portion 32 and into the single output channel 62 of the output portion 34.

Figure 4:
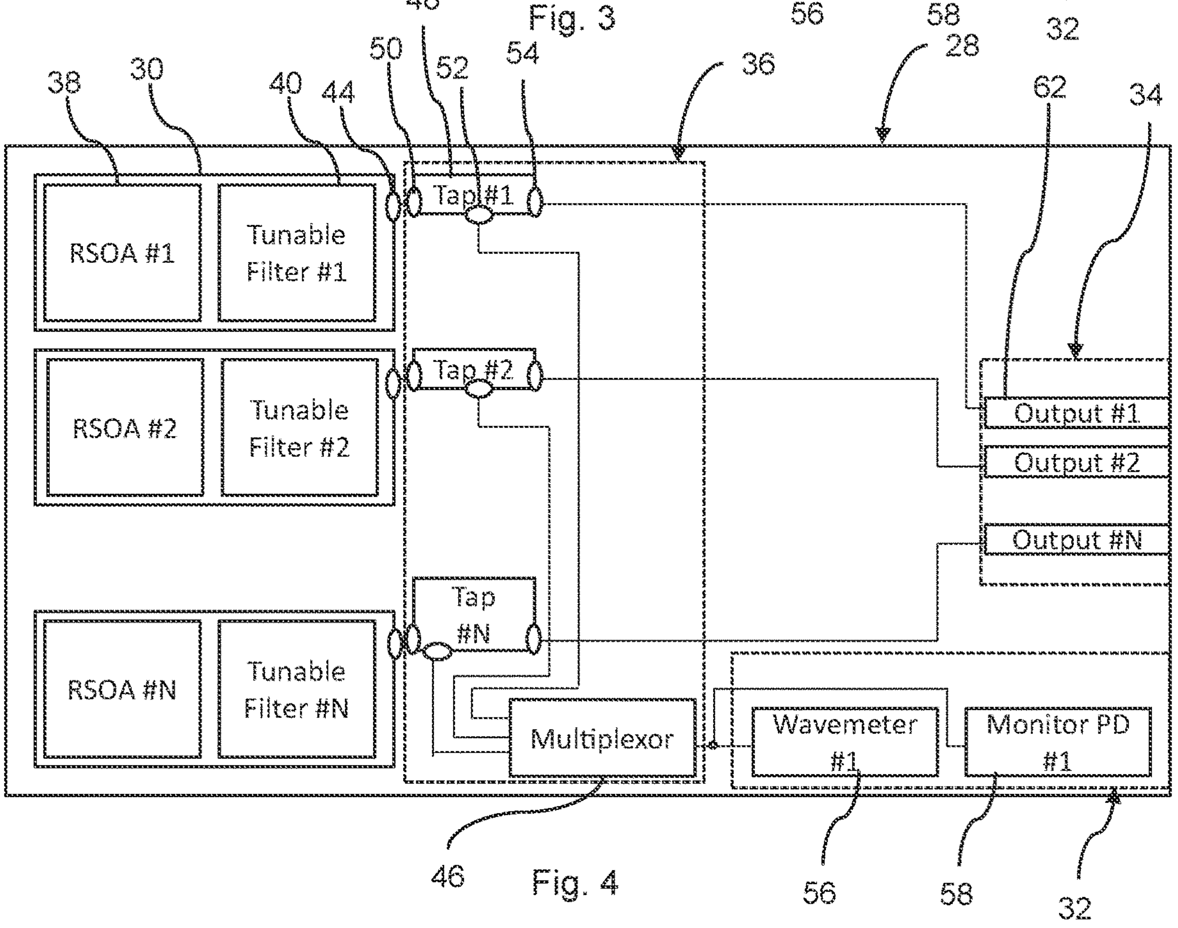
FIG. 4 shows a block diagram of the components of a third embodiment of the photonic integrated circuit arranged in the wearable device.

The embodiment depicted in FIG. 4 has the same configuration as the embodiment depicted in FIG. 2 except for the following differences.

The splitting/combining portion 36 includes a single optical combiner 46 and n optical splitters 48. The measuring portion 32 includes a single wavemeter 56 and a single photodetector 58. The output portion 34 includes n output channels 62 (similar to the configuration depicted in FIG. 2). Each of the n optical splitters 48 is optically coupled to a respective tunable laser 30 and splits the light received from the respective tunable laser 30 to the respective optical combiner 46 and to the respective output channel 62 of the output portion 34. The optical combiner 46 combines the light received by the n optical splitters 48 and outputs the multiplexed light to the measuring portion 32.

Figure 5:
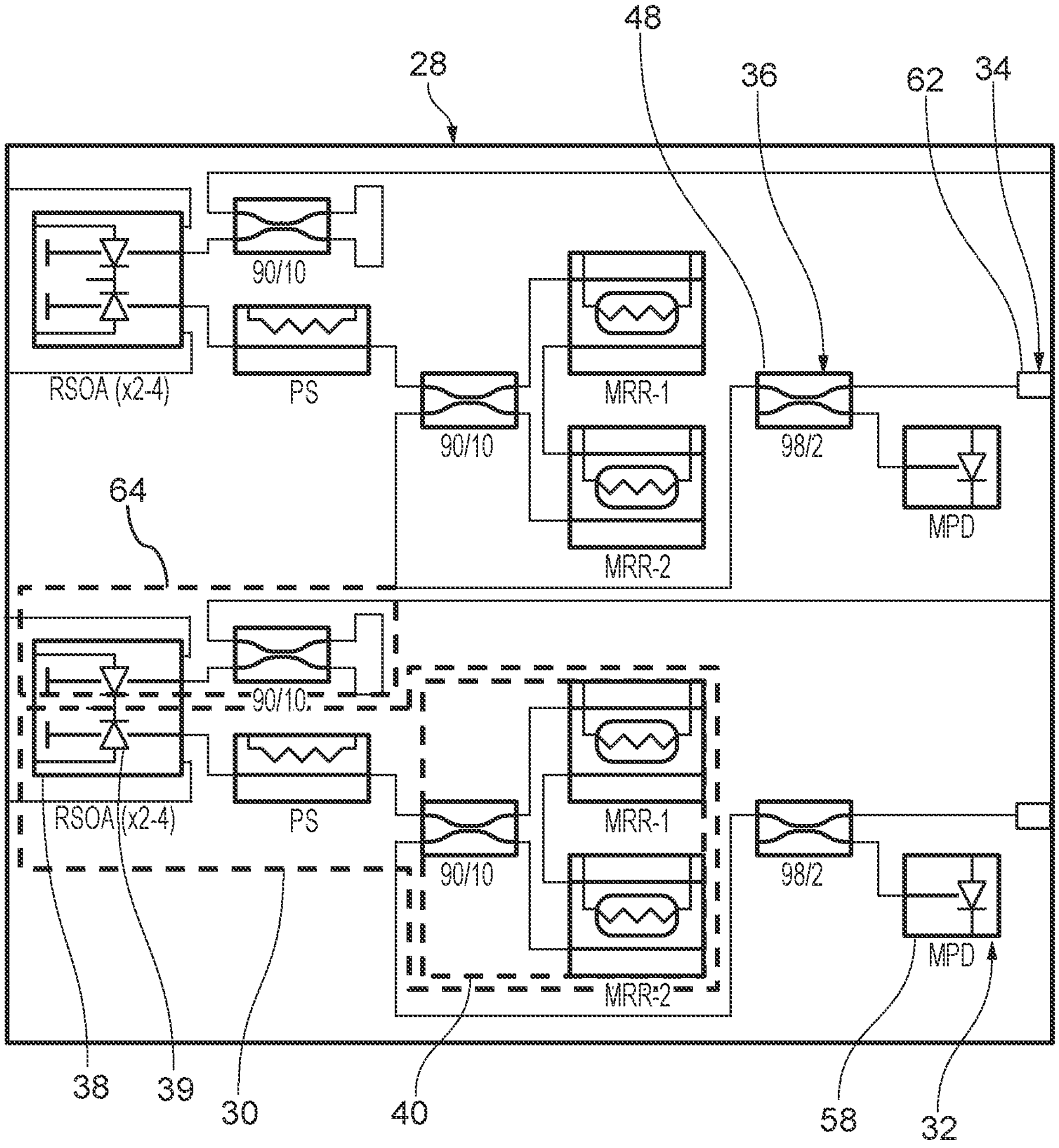
FIG. 5 shows a schematic drawing of a fourth embodiment of the photonic integrated circuit arranged in the wearable device.

The embodiment depicted in FIG. 5 has the same configuration as the embodiment depicted in FIG. 2 except for the following differences.

The PIC 28 includes only two tunable lasers 30. The two measurement portions 32 each include only the photodetector 58. Each of tunable lasers 30 further includes a Fabry-Perot laser 64 which generates light that is output by a different waveguide/output compared to the output portion 34. The Fabry-Perot laser 64 is included for diagnostic purposes, but is not essential for the overall function of the PIC 28. The numbers depicted in FIG. 5 along the optical splitters 48 indicate the ratio of intensity that is output at the output channels.

Figure 6:
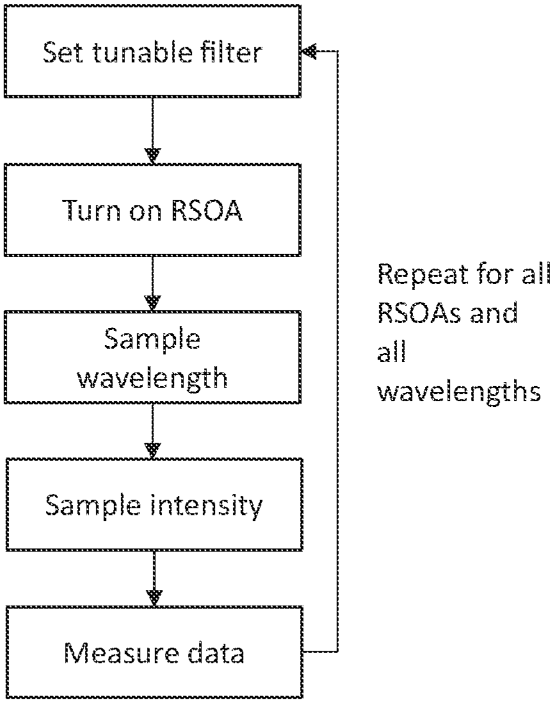
FIG. 6 shows a block diagram indicating steps of a first embodiment of method for controlling the photonic integrated circuit arranged in the wearable device.

FIG. 6 depicts steps for operating the wearable device 10. The tuning element 40 for the first tunable laser 30 (tunable laser #1) is set according to predetermined values, such as to a look-up table of pre-calibrated set points, followed by turning on the first photodiode 39/RSOA 40, then sampling wavelength and intensity while data is collected at the light detector 18. This is repeated for all wavelengths of the tunable lasers range and all tunable lasers 30 on the PIC 28.

Figure 7:
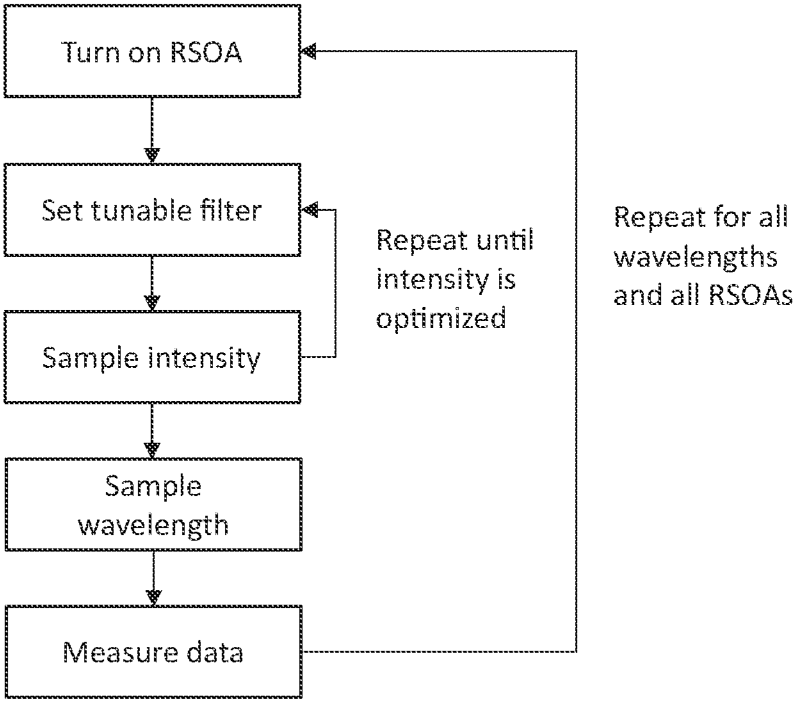
FIG. 7 shows a block diagram indicating steps of a second embodiment of method for controlling the photonic integrated circuit arranged in the wearable device.

FIG. 7 depicts steps for operating the wearable device 10. The first photodiode 39/RSOA 40 (RSOA #1, i.e. the photodiode 39/RSOA 40 of tunable laser #1) is turned on, the tuning element 40 is then set and optimized in real time (using the measurement results generated by the measurement portion 32). Then wavelength and intensity are sampled while data is collected at the light detector 18. The first photodiode 39/RSOA 40 is turned off after cycling through all wavelengths within its range. This is repeated for all other tunable lasers 30 on the PIC 28.

Figure 8:
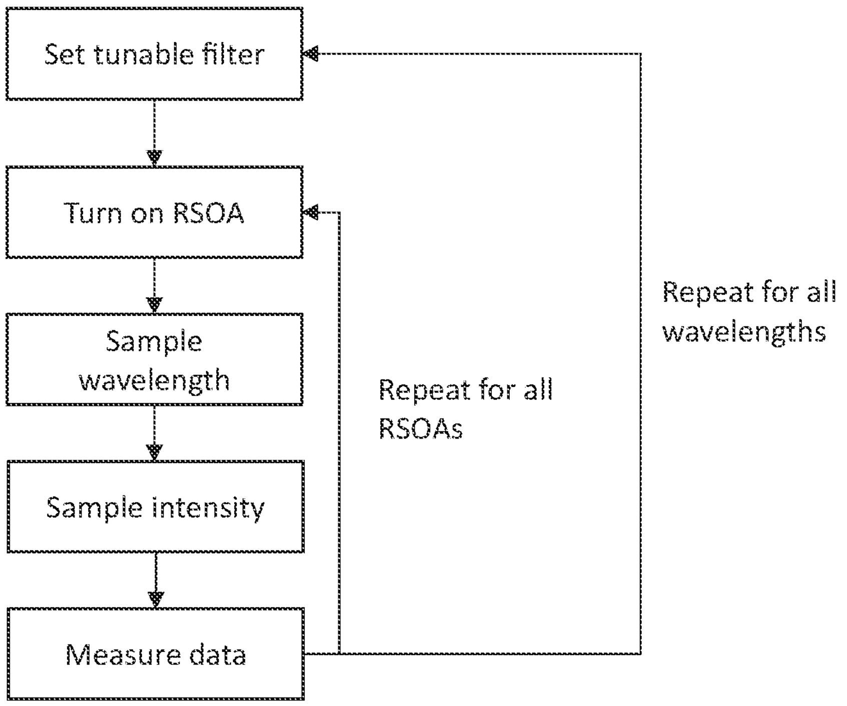
FIG. 8 shows a block diagram indicating steps of a third embodiment of method for controlling the photonic integrated circuit arranged in the wearable device.

FIG. 8 depicts steps for operating the wearable device 10. In this case, the tuning elements 40 for all tunable lasers 30 are wired in parallel. The tuning elements 40 are set for all tunable lasers 30 simultaneously, then the first photodiode 39/RSOA 40 (RSOA #1, i.e. the photodiode 39/RSOA 40 of tunable laser #1) is turned on while sampling wavelength and intensity with data collection at the light detector 18. This is then repeated for all other photodiode 39/RSOAs 40 before setting the tuning elements 40 again and repeating for all wavelengths.

Figure 9:
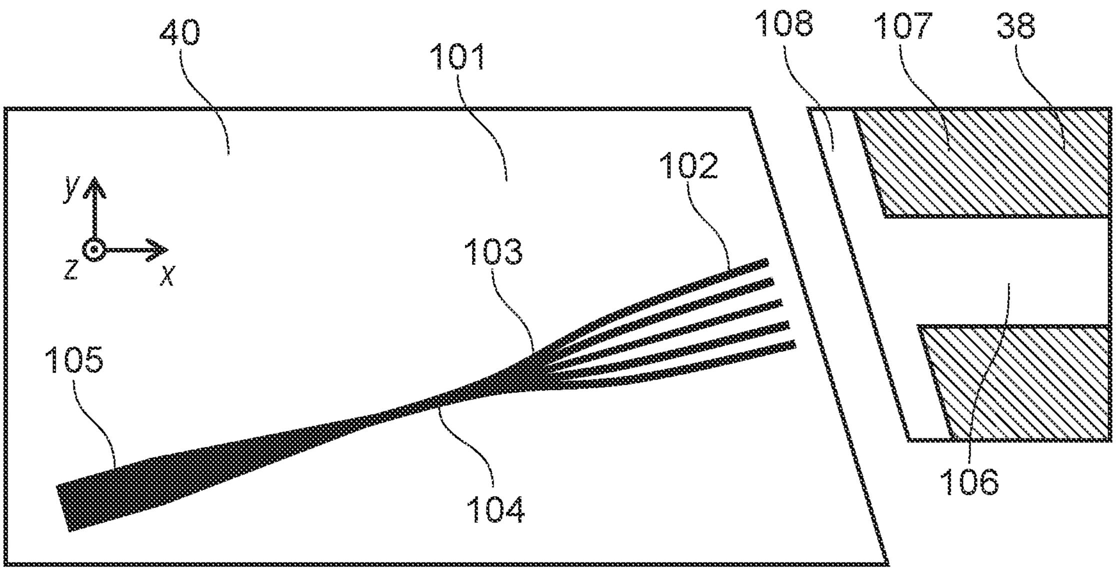
FIG. 9 shows a schematic top-view of an optical coupler.

FIG. 9 is a top view of an optical coupler providing a transition part between an RSOA 38 (an example of the first optical element) and a PIC SiN waveguide (an example of a second optical element which may include the tunable filter 40). The RSOA 38 is electrically driven, and it is made of a ridge structure patterned on top of a multiple quantum wells (MQWs) with an optional width of 2 μm. A narrow unetched part is left in a facet 108 of RSOA 38 which provides the first waveguide 106, which may include T-bar. The T-bar can help protect the facet 108 from damages that can happen during the bonding process which is an example for fixing the RSOA 38 to the tunable filter 40. The width of the T-bar can be 1 μm. The facet 108 of RSOA 38 has a first angle with respect to a direction of extension of the first waveguide 106 (optionally between 80° and 84°), which is designed to minimize the back-reflection into the RSOA 38.

On the other side, the PIC or the tunable filter 40 can include a plurality of nanobeams 102, a merging section 103, a tapered portion 104, and a second waveguide 105. The nanobeams 102, the merging section 103, the tapered portion 104, and the waveguide 105 can be made from $SiN_4$ and/or can be covered by a material 101, such as silicon dioxide. Each nanobeam 102 has a width and height of 700 nm and 400 nm, respectively. These dimensions allow a single mode operation.

The tapered portion 104 has a width corresponding to the width of a nanobeam 102. There is a spacing between nanobeams 102 and the edge of PIC 40 that is filled by $SiO_2$ 101. An refractive index of fluid, which is used for bonding process of the RSOA 38 to the tunable filter 40, is very close to the index of the SiO2 101. The fluid can be a glue that is provided between the RSOA 38 and the tunable filter 40 (not shown in FIG. 9).

Each nanobeam 102 has a straight section and a curved section. The nanobeams 102 are arranged to provide a fork design with five nanobeams 102. The advantage of this configuration is in part that there is a super-mode distributed over two or more nanobeams 102 rather than a single mode confined in one nanobeam 102. The size and shape of the super-mode is controllable by the number and dimensions of nanobeams 102.

Figure 11:
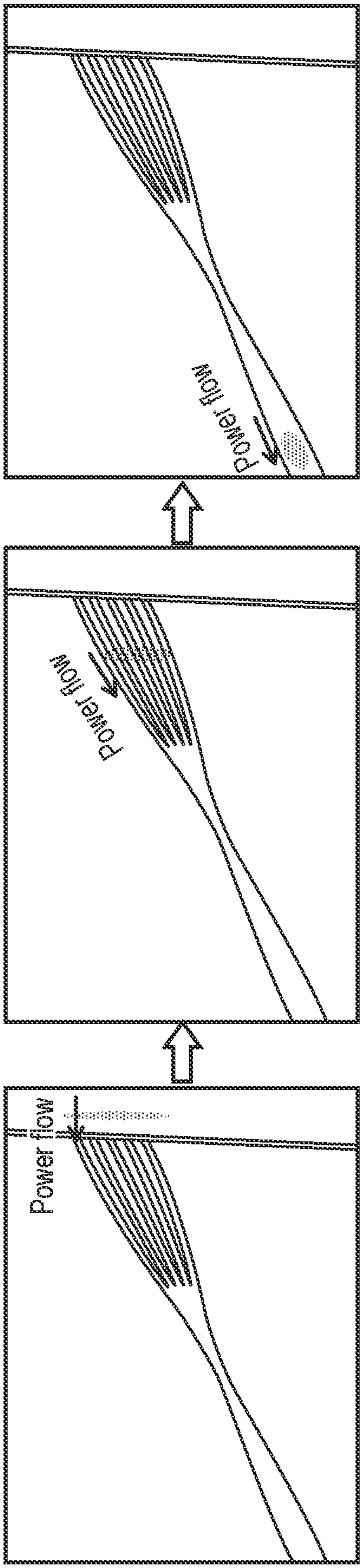
FIG. 11 shows snap shots of a transition of light in the optical coupler of FIG. 9.

The propagation from the first waveguide 106 via the nanobeams 102 to the second waveguide 105 is shown in FIG. 11. It is immediately apparent form FIG. 11 that small offsets of the first waveguide 106 with respect to the nanobeams 102 along the direction of the facet 108 (due to inaccuracies when fixing the RSOA 38 to the tunable filter 40) do not significantly affect the propagation of the light in the nanobeams 102. The super-mode in the nanobeams 102 is essentially in the middle three nanobeams 102 so that an small offset results in a shift of the super-mode to upper three or lower three nanobeams 102.

In this embodiment, there is one nanobeam 102 at the center, and two sets of double nanobeams 102 with identical distances from the middle nanobeam 102. The nanobeams 102 of number 2 and 4, and the nanobeams 102 of number 1 and 5 form Y-combiner with each other. Two Y-combiners have a same joint point along the middle nanobeam 102 (i.e., number 3). The y-span of the outer Y-combiner is double of the inner Y-combiner. The widths of all nanobeams 102 are chosen to be the same. While the facet angle of PIC 40 is the same as the facet angle of RSOA 38, but the fork coupler has an extra angle in order to match with the angle of the incoming light from RSOA 38. When the light exists from the RSOA facet 108, it experiences a bending angle with respect to the facet 108 due the index change according to the Snell's law. This extra angle can be considered to maximize the coupling efficiency. The facet angle for both RSOA 38 and PIC 40 are optimized to 8°. Additionally, fork coupler has an extra 9° angle so that the nanobeams 102 form an angle of 81° with the side surface of the tunable filter 40.

Figure 10:
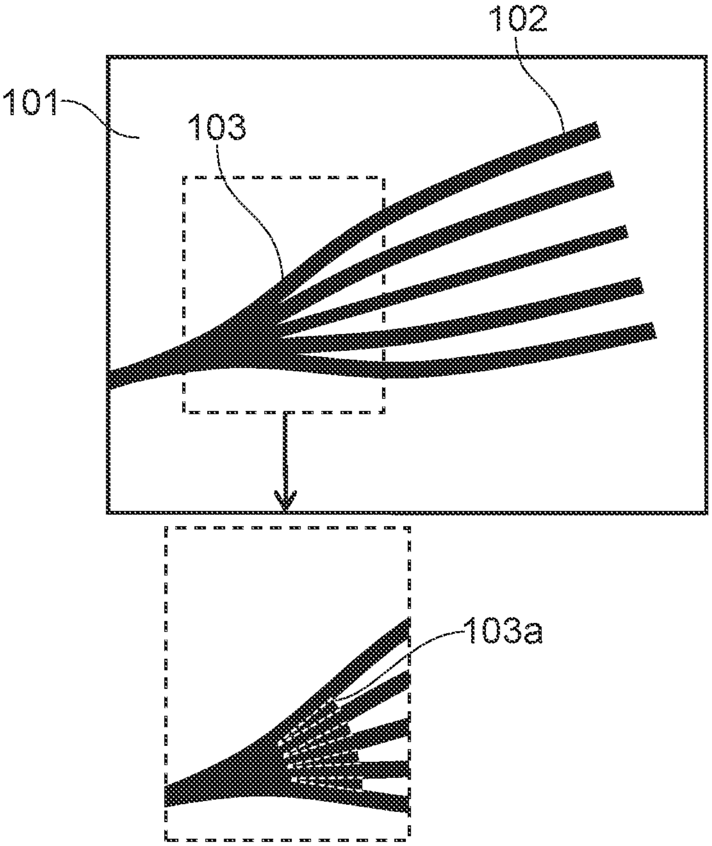
FIG. 10 shows an enlarged schematic top-view of a tapered portion, a merging section, and nanobeams of the optical coupler of FIG. 9.

FIG. 10 shows the transition between nanobeams 102 and the merging section 103. It is readily visible from the enlarged image in FIG. 10 that the merging section 103 includes filler portions 103*a* (indicated by the dashed lines in FIG. 10) which fill spaces between the nanobeams 102. Without the filler portions 103*a*, the nanobeams 102 would merge closer to the tapered portion 104. The filler portions 103*a* are present due manufacturing constraints which do not provide very small distances between the nanobeams 102 which would be present with the spaces occupied by the filler portions 103*a*.

The invention claimed is:

1. A device, comprising:

at least one laser, a first laser of the at least one laser being configured to generate light having a wavelength below 1200 nm;

an output port configured to output the light to a portion of a tissue of a user;

a measuring portion including a measuring port, the measuring port being connected to at least one detector, and configured to measure optical information of speckle and an intensity of light received from the tissue at the measuring port; and a processor configured to measure speckleplethysmography and photoplethysmography based on the optical information, wherein the first laser includes a ring resonator laser, a laser configured to generate light having a fixed wavelength, a laser being constructed using hybrid integration, and/or a tunable laser, wherein the at least one laser comprises n lasers, n being an integer greater than or equal to 2 and each laser having a laser output, and wherein the device comprises a splitting/combining portion including n input ports, a first output port, and a second output port, each input port being coupled to a respective one of the laser outputs, the first output port of the splitting/combining portion being coupled to the measuring port, and the second output port of the splitting/combining portion being coupled to the output port of the device.

2. The device of claim 1, wherein the splitting/combining portion includes n optical splitters, each optical splitters being coupled to a respective one of the n input ports, a respective first output port, and a respective second output port, and wherein the output port includes n output channels, each output channel being coupled to a respective one of the second output ports.

3. The device of claim 1, wherein the splitting/combining portion includes one optical combiner and one optical splitter, the optical combiner being coupled to the n input ports for combining the light of the n lasers, the optical splitter being coupled to the optical combiner, to the first output port, and the second output port for splitting the light received from the optical combiner into the first output port and the second output port, and wherein the output port includes one output channel that is coupled to the optical splitter.

4. The device of claim 1, wherein the splitting/combining portion includes n optical splitters and one optical combiner, wherein each optical splitter is coupled to a respective one of the n input ports, the one optical combiner and to the second output port for splitting the light received from the respective laser into the optical combiner and the second output port, and wherein the optical combiner is coupled to the measuring portion for combining the light received from the n optical splitters, and wherein the output port includes n output channels, each output channel being coupled to a respective one of the optical splitters.

5. The device of claim 1, further comprising a control portion coupled to the n lasers and the measuring portion for tuning the n lasers based on the intensity measured by the measuring portion, wherein the control portion is configured to tune all n tunable lasers using a common tuning algorithm.

6. The device of claim 1, wherein the first laser is a tunable laser and includes a reflective semiconductor optical amplifier (RSOA) and a tuning element, wherein the tuning element includes a micro-ring reflector and/or a sampled Distributed Bragg Reflector (DBR) grating, and wherein the tunable laser includes phase control section coupled between the RSOA and the tuning element for determining the phase of light.

7. The device of claim 1, comprising a waveguide core made from silicon nitride ($Si_3N_4$), wherein the first laser is configured to generate light having a wavelength below 1000 nm.

8. The device of claim 1, wherein the device is configured to execute diffuse correlation spectroscopy (DCS), and/or wherein the device is configured to execute a measurement of pulse oximetry (SpO2), oxygen saturation, carboxy haemoglobin, methaemoglobin, or fractional oxygen saturation.

9. The device of claim 1, wherein the device is a wearable device.

10. A method for controlling the device of claim 1, the method comprising:

a) setting a tuning element of the first laser, b) turning the first laser on to generate the light by the first laser, c) measuring the optical information of the light received from the tissue, and d) analysing the optical information to determine blood flow of the user.

11. The device of claim 1, further comprising an optical coupler, comprising:

a first optical element including a first waveguide, the first waveguide including a facet configured to emit electromagnetic radiation from the first optical element, a second optical element including a second waveguide and an end portion configured to couple electromagnetic radiation into the second optical element, wherein the first optical element and the second optical element are fixed so that the facet faces the end portion, wherein the end portion includes a plurality of nanobeams, each nanobeam having a width that is smaller than a width of the second waveguide, wherein the end portion includes a merging section at which the nanobeams merge, and wherein the second optical element further includes a tapered portion arranged between the merging section and the second waveguide, a minimal width of the merging section is smaller than the width of the second waveguide.

12. The device of claim 11, wherein the width of each of the nanobeams is constant and respective sections of the plurality of nanobeams extend parallel to each other, and/or wherein a first angle between a direction of extension of the first waveguide and a plane of the facet is between 80° and 84°.

13. The device of claim 12, wherein a side surface of the second optical element extends parallel to the facet, wherein a second angle between a direction of extension of the parallel sections of the plurality of nanobeams and a plane of the side surface is between 79° and 83°.

14. The device of claim 13, wherein the end portion is spaced apart from the side surface of the second optical element, and wherein a space between the side surface and the end portion is filled with $SiO_2$.

15. The device of claim 11, wherein the first waveguide includes a T-bar providing the facet.

16. A device, comprising:

at least one laser, a first laser of the at least one laser being configured to generate light having a wavelength below 1200 nm;

an output port configured to output the light to a portion of a tissue of a user;

a measuring portion including a measuring port, the measuring port being connected to at least one detector, and configured to measure optical information of speckle and an intensity of light received from the tissue at the measuring port; and a processor configured to measure speckleplethysmography and photoplethysmography based on the optical information, wherein a laser output of the first laser is configured to split the light generated by the first laser into a first optical component and a second optical component, wherein the first optical component is to be transmitted to the portion of tissue of the user, wherein each of the at least one detector is configured to receive a speckle pattern from the tissue responsive to the first optical component, wherein the device further comprises one or more optical splitters configured to optically couple the second optical component to one or more respective input(s) of the at least one detector, and wherein the device is further adapted to measure interference at the at least one detector between a sample arm formed by the first optical component and a reference arm formed by the second optical component.

17. A device, comprising:

at least one laser, a first laser of the at least one laser being configured to generate light having a wavelength below 1200 nm;

an output port configured to output the light to a portion of a tissue of a user;

a measuring portion including a measuring port, the measuring port being connected to at least one detector, and configured to measure optical information of speckle and an intensity of light received from the tissue at the measuring port;

a processor configured to measure speckleplethysmography and photoplethysmography based on the optical information; and a homogenizer, the homogenizer comprising a planar waveguide device configured to receive light from the first laser and to generate interference to produce multiple statistically uncorrelated speckle patterns that are combined to provide the light at the output port.

* * * * *